US012594089B2

(12) United States Patent
Ebersole et al.

(10) Patent No.: US 12,594,089 B2
(45) Date of Patent: Apr. 7, 2026

(54) MEDICAL TOOLS FOR AND METHODS OF GAINING ACCESS TO EXTRAVASCULAR SPACES

(71) Applicant: Medtronic, Inc., Minneapolis, MN (US)

(72) Inventors: Garrett P. Ebersole, Hamden, CT (US); Kyle R. Marquard, Lino Lakes, MN (US); Krishnakumar Somasundaram, Kovaipudur (IN); Stanislaw Z. Marczyk, Stratford, CT (US); Linnea R. Lentz, Stacy, MN (US); Olesea Diaz-Chiosa, Naugatuck, CT (US); Christopher Switalski, Glastonbury, CT (US)

(73) Assignee: Medtronic, Inc., Minneapolis, MN (US)

( * ) Notice: Subject to any disclaimer, the term of this patent is extended or adjusted under 35 U.S.C. 154(b) by 934 days.

(21) Appl. No.: 17/544,399

(22) Filed: Dec. 7, 2021

(65) Prior Publication Data

US 2022/0168007 A1     Jun. 2, 2022

Related U.S. Application Data

(63) Continuation of application No. 16/052,280, filed on Aug. 1, 2018, now Pat. No. 11,197,687.

(51) Int. Cl.
*A61B 17/32*          (2006.01)
*A61B 17/34*          (2006.01)
          (Continued)

(52) U.S. Cl.
CPC .......... *A61B 17/32* (2013.01); *A61B 17/3468* (2013.01); *A61N 1/372* (2013.01);
          (Continued)

(58) Field of Classification Search
CPC .......... A61B 18/02; A61B 2017/00084; A61B 2018/0237; A61B 2505/09; A61B 5/01;
          (Continued)

(56) References Cited

U.S. PATENT DOCUMENTS 5,331,950 A     7/1994 Wood, Sr.
5,401,272 A     3/1995 Perkins
          (Continued)

OTHER PUBLICATIONS

6996T Tunneling Tool, Medtronic, Inc. Technical Manual, 12 pp., 2011. (Applicant points out, in accordance with MPEP 609.04(a), that the year of publication is sufficiently earlier than the effective U.S. filing date so that the particular month of publication is not in issue.).
          (Continued)

*Primary Examiner* — Tigist S Demie
(74) *Attorney, Agent, or Firm* — Shumaker & Sieffert, P.A.

(57)          ABSTRACT

In some examples, a tool for, e.g., creating a sub-sternal tunnel in a patient or other use, is described. The tool may include a handle and a tunneling shaft coupled to the handle. The tunneling shaft extends from a proximal end to a distal end, and at least a portion of the tunneling shaft extends in a curved orientation between the first end to the distal end. The distal end of the tunneling shaft includes a cutting tool having a sharp edge. The cutting tool is moveable from a recessed position in which the sharp edge of the cutting tool is recessed into the distal end of the tunneling shaft to a deployed position in which the sharp edge of the cutting tool extends beyond the distal end of the tunneling shaft in the deployed position, e.g., to cut pericardium, scar tissue, and/or connective tissue with the sharp edge.

20 Claims, 21 Drawing Sheets

(51) Int. Cl.

| | |
|---|---|
| *A61N 1/372* | (2006.01) |
| *A61M 25/01* | (2006.01) |
| *A61N 1/362* | (2006.01) |
| *A61N 1/39* | (2006.01) |

(52) U.S. Cl.
CPC ............. *A61B 2017/320044* (2013.01); *A61B 2017/320056* (2013.01); *A61M 25/0194* (2013.01); *A61N 1/362* (2013.01); *A61N 1/39622* (2017.08)

(58) Field of Classification Search
CPC ....... A61B 5/015; A61B 5/486; A61B 5/7425; A61F 2007/0001; A61F 2007/0054; A61F 2007/0056; A61F 2007/0076; A61F 2007/0086; A61F 2007/0093; A61F 2007/0095; A61F 2007/0288; A61F 2007/0295; A61F 7/0085; A61F 7/02
See application file for complete search history.

(56) References Cited

U.S. PATENT DOCUMENTS

| | | | |
|---|---|---|---|
| 5,435,805 A | | 7/1995 | Edwards et al. |
| 5,441,498 A | * | 8/1995 | Perkins .............. A61B 18/1442 604/35 |
| 5,445,142 A | | 8/1995 | Hassler, Jr. et al. |
| 5,549,601 A | * | 8/1996 | McIntyre ............... A61B 18/24 606/14 |
| 5,632,717 A | | 5/1997 | Yoon |
| 5,672,153 A | | 9/1997 | Lax et al. |
| 5,697,909 A | | 12/1997 | Eggers et al. |
| 5,810,764 A | | 9/1998 | Eggers et al. |
| 5,993,466 A | | 11/1999 | Yoon |
| 5,993,467 A | | 11/1999 | Yoon |
| 6,196,968 B1 | | 3/2001 | Rydin et al. |
| 6,494,827 B1 | | 12/2002 | Matsumoto et al. |
| 6,685,630 B2 | | 2/2004 | Sauer et al. |
| 7,470,230 B2 | | 12/2008 | Smith et al. |
| 9,289,232 B2 | | 3/2016 | Massengale et al. |
| 9,610,436 B2 | | 4/2017 | Seifert et al. |
| 9,618,360 B2 | | 4/2017 | Brown et al. |
| 10,531,893 B2 | | 1/2020 | Seifert et al. |
| 10,695,089 B2 | | 6/2020 | Malewicz et al. |
| 11,197,687 B2 | | 12/2021 | Ebersole et al. |
| 2002/0029060 A1 | | 3/2002 | Hogendijk |
| 2002/0068930 A1 | | 6/2002 | Tasto et al. |
| 2002/0095152 A1 | | 7/2002 | Ciarrocca et al. |
| 2002/0120259 A1 | | 8/2002 | Lettice et al. |
| 2004/0006339 A1 | | 1/2004 | Underwood et al. |
| 2005/0203561 A1 | | 9/2005 | Palmer et al. |
| 2009/0234427 A1 | | 9/2009 | Chinn et al. |
| 2009/0254095 A1 | | 10/2009 | Levine et al. |
| 2010/0048994 A1 | | 2/2010 | Okoniewski |
| 2010/0318098 A1 | | 12/2010 | Lund et al. |
| 2012/0330292 A1 | | 12/2012 | Shadduck et al. |
| 2014/0114300 A1 | | 4/2014 | Orczy-Timko et al. |
| 2014/0350338 A1 | | 11/2014 | Tanaka et al. |
| 2015/0073449 A1 | | 3/2015 | Nallarkrishnan |
| 2015/0133953 A1 | | 5/2015 | Seifert et al. |
| 2015/0306375 A1 | | 10/2015 | Marshall et al. |
| 2015/0306410 A1 | | 10/2015 | Marshall et al. |
| 2015/0342627 A1 | | 12/2015 | Thompson-Nauman et al. |
| 2016/0015406 A1 | | 1/2016 | Ohki |
| 2016/0158567 A1 | | 6/2016 | Marshall et al. |
| 2017/0007287 A1 | | 1/2017 | Malewicz et al. |
| 2017/0020551 A1 | * | 1/2017 | Reddy ............... A61B 17/0218 |
| 2017/0100148 A1 | | 4/2017 | De Kock et al. |
| 2018/0000316 A1 | | 1/2018 | Yamada |
| 2018/0280084 A1 | | 10/2018 | Hancock et al. |
| 2019/0298406 A1 | * | 10/2019 | Lee ............... A61B 17/320016 |
| 2019/0374285 A1 | | 12/2019 | Hancock et al. |
| 2020/0038048 A1 | | 2/2020 | Ebersole et al. |
| 2020/0060534 A1 | | 2/2020 | Tabe et al. |
| 2020/0360085 A1 | | 11/2020 | Hancock |
| 2022/0160425 A1 | | 5/2022 | Doll et al. |

OTHER PUBLICATIONS

Athanasiou et al., "Video Assisted Resternotomy in High-Risk Redo Operations—the St. Mary's Experience," European Journal of Cardiothoracic Surgery, vol. 21, Jan. 31, 2002, pp. 932-934.
(PCT/US2019/004273) PCT Notification of Transmittal of the International Search Report and the Written Opinion of the International Searching Authority, mailed Oct. 23, 2019, 13 pages.
Guenther et al., "Substernal Lead Implantation: A Novel Option to Manage DFT Failure in S-ICD Patients," Clinical Research in Cardiology, vol. 104, No. 2, Oct. 2014, pp. 189-191.
Lambiase et al., "Worldwide Experience with a Totally Subcutaneous Implantable Defibrillator: Early Results from the Effortless S-ICD Registry," European Heart Journal, Mar. 26, 2014, 10 pp.
Prosecution History from U.S. Appl. No. 16/052,280, dated Mar. 20, 2020 through Aug. 18, 2021, 90 pp.
Communication pursuant to Article 94(3) EPC from counterpart European Application No. 19752820.1 dated Jun. 26, 2024, 6 pp.

* cited by examiner

FIG. 7A                                     FIG. 7B

MEDICAL TOOLS FOR AND METHODS OF GAINING ACCESS TO EXTRAVASCULAR SPACES

This application is a continuation of U.S. patent application Ser. No. 16/052,280, filed Aug. 1, 2018, now U.S. Pat. No. 11,197,687, the entire content of which is incorporated herein by reference.

TECHNICAL FIELD

The present disclosure pertains to tools and associated methods for safely gaining access to spaces within patient, and more particularly to those suited to safely gain access into a sub-sternal or other extravascular space for the positioning of a medical device therein.

BACKGROUND

Some medical procedures may include crossing multiple tissue layers to gain access to a location within the body of a patient. Such medical procedures may include implanting one or more medical devices or components thereof, e.g., medical electrical leads, at the location. One manner of accessing an intrathoracic location is substernally and includes traversing one or more layers of tissue, e.g., diaphragmatic attachments that attach the diaphragm to the sternum. An example of a procedure is the implantation of the distal portions of one or more leads substernally, and may include using an implant tool to access the intrathoracic cavity of the patient. The one or more leads may be part of an implantable cardiac defibrillator (ICD) system that may be used to deliver high-energy electrical pulses to the patient's heart to terminate life threatening cardiac arrhythmias, such as ventricular fibrillation. Such ICDs may include, or may be part of a system that includes, a subcutaneously-implantable housing that encloses a pulse generator or other electronics of an ICD. The housing of some ICDs may be connected to the one or more leads, which may be configured to deliver defibrillation and/or pacing pulses.

SUMMARY

This disclosure provides tools and implant techniques utilizing such tools to gain access and implant medical devices or components thereof within spaces within a patient, e.g., a lead within an extravascular space. In one example, this disclosure provides a tool for creating a sub-sternal tunnel in a patient. The tool comprises a handle; and a tunneling shaft coupled to the handle, wherein the tunneling shaft extends from a proximal end to a distal end, and at least a portion of the tunneling shaft extends in a curved orientation between the first end to the distal end, wherein the distal end of the tunneling shaft includes a cutting tool having a sharp edge, the cutting tool moveable from a recessed position in which the sharp edge of the cutting tool is recessed into the distal end of the tunneling shaft to a deployed position in which the sharp edge of the cutting tool extends beyond the distal end of the tunneling shaft in the deployed position.

In another example, this disclosure is directed to a method, e.g., for creating tunnel in a patient with a tool. The method inserting a distal portion of a tool in a patient through an incision in the patient, wherein the tool comprises a handle; and a tunneling shaft coupled to the handle, wherein the tunneling shaft extends from a proximal end to a distal end, and at least a portion of the tunneling shaft extends in a curved orientation between the first end to the distal end, wherein the distal end of the tunneling shaft includes a cutting tool having a sharp edge, the cutting tool moveable from a recessed position in which the sharp edge of the cutting tool is recessed into the distal end of the tunneling shaft to a deployed position in which the sharp edge of the cutting tool extends beyond the distal end of the tunneling shaft in the deployed position; and deploying the cutting tool from the recessed position to the deployed position, while the distal portion of the tool is inserted in the patient through the incision, to cut a tissue of the patient with the sharp edge of the cutting tool.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

The following drawings are illustrative of example embodiments and do not limit the scope of the invention. The drawings are not to scale (unless so stated) and are intended for use in conjunction with the explanations in the following detailed description. Examples will hereinafter be described in conjunction with the appended drawings wherein like numerals denote like elements.

FIGS. 7A-7C are schematic diagrams illustrating the distal portion of another example tunneling tool according to an example of the disclosure.

The details of one or more examples of this disclosure are set forth in the accompanying drawings and the description below. Other features, objects, and advantages of this disclosure will be apparent from the description and drawings, and from the claims.

DETAILED DESCRIPTION

The following detailed description is exemplary in nature and is not intended to limit, in any way, the scope, applicability, or configuration of the tools and techniques described in this disclosure. Rather, the following description provides practical examples, and those skilled in the art will recognize that some of the examples may have suitable alternatives.

Figure 1A:
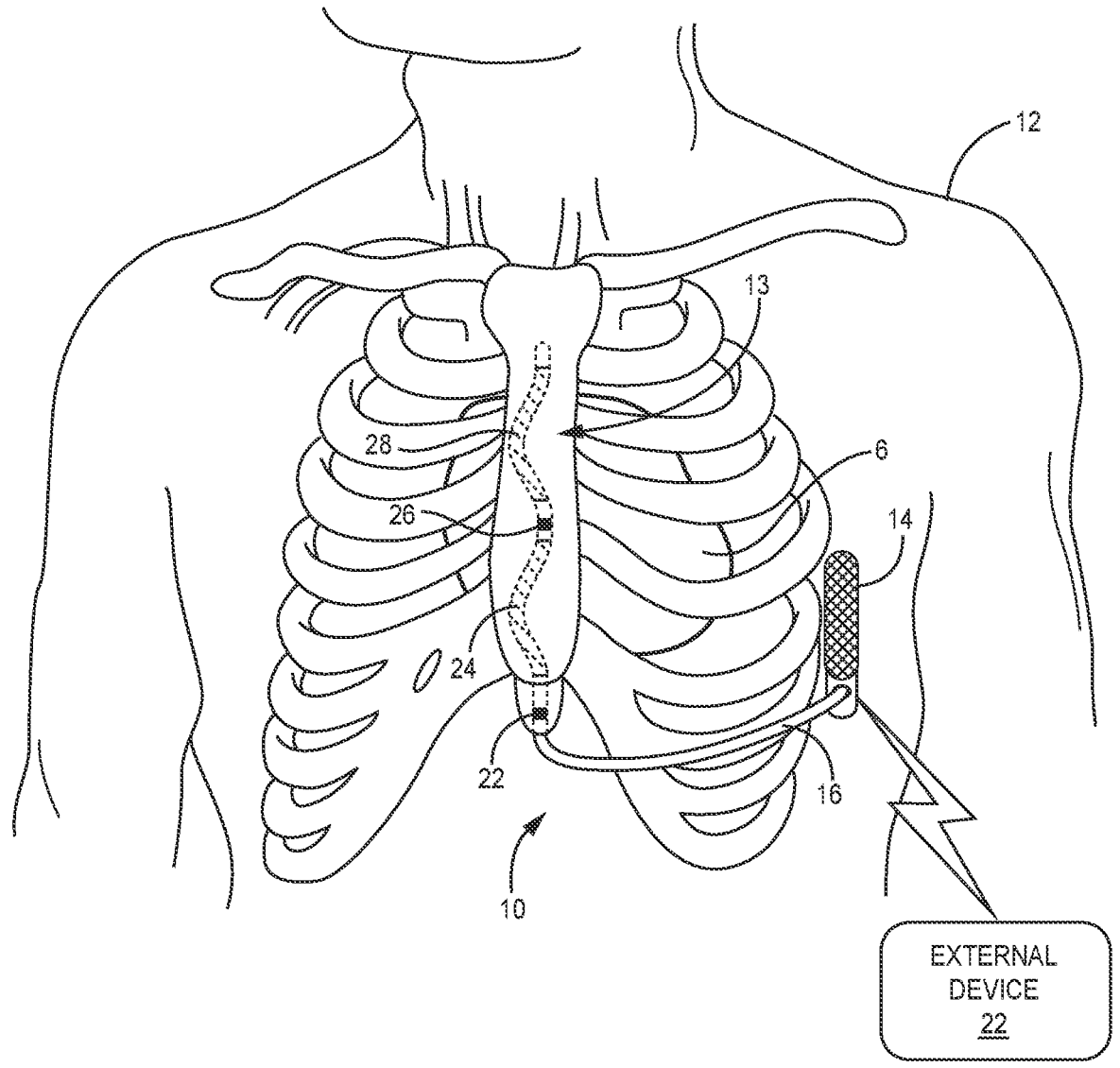
FIGS. 1A-B are schematics showing an exemplary extravascular implant.
Figure 1B:
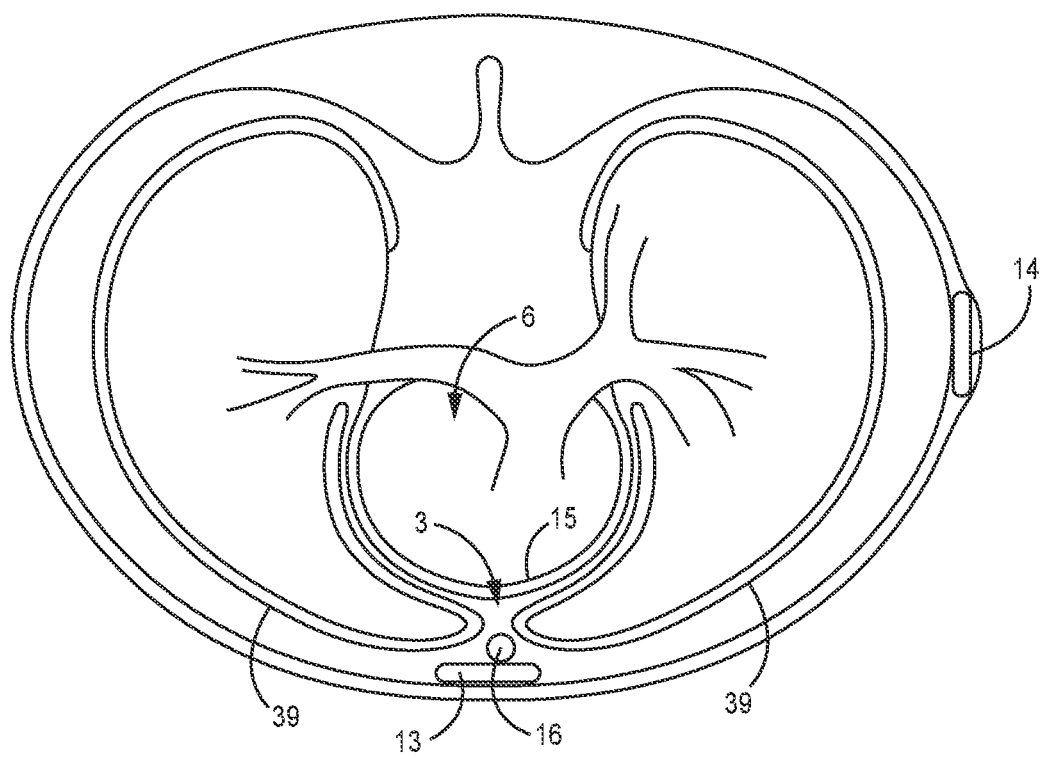

FIGS. 1A-B are schematics showing an exemplary extravascular implant of an exemplary system 10 that includes a pulse generator 14 and an implantable medical electrical lead 16 coupled thereto. Pulse generator 14 is shown implanted subcutaneously on the left mid-axillary of a patient 12, superficially of the patient's ribcage. Pulse generator 14, which may be configured to provide cardiac pacing and/or defibrillation therapy, includes a hermetically sealed housing in which the appropriate electronics and a power supply are contained, and which is formed from a conductive material, such as titanium, or from a combination of conductive and non-conductive materials. Pulse generator 14 further includes a connector module by which lead 16 is electrically coupled to the electronics contained therein, for example, by electrical contacts contained within the connector module and a corresponding hermetically sealed feedthrough assembly, such as is known in the art. The conductive material of device housing may be employed as an electrode, for example, to provide the aforementioned therapy in conjunction with one or more pace/sense electrodes 22, 26 and/or defibrillation electrodes 24, 28 of lead 16, which is shown implanted in a sub-sternal space 3, for example, within the loose connective tissue and/or sub-sternal musculature of the anterior mediastinum.

Lead 16 may have any of a number of configurations. For example, lead 16 may include more or fewer pace/sense electrodes. In another example, lead 16 may include more or less than two defibrillation electrodes 24, 28 and/or have a defibrillation electrode(s) that is formed of multiple segments. Examples of leads with multiple defibrillation electrodes and/or segments are described in commonly assigned, co-pending U.S. Patent Publication No. 2015/0306375 (Marshall et al.), U.S. Patent Publication No. 2015/0306410 (Marshall et al.) and U.S. Patent Publication No. 2016/0158567 (Marshall et al.), each of which is incorporated herein by reference in its entirety.

With reference to FIG. 1B, the sub-sternal space 3 may be viewed as being bounded laterally by pleurae 39 that enclose the patient's lungs, posteriorly by the pericardial sac 15 that encloses the patient's heart 6, and anteriorly by the sternum 13. In some instances, the anterior wall of the anterior mediastinum may also be formed by the transversus thoracis and one or more costal cartilages. Although FIGS. 1A and

1B are described in the context of the distal portion of lead 16 being placed within the sub-sternal space 3, in other examples, the tools and implant techniques described herein may be used to implant a distal portion of the lead 16 at other locations outside the heart. In one example, the tools may be used to place the distal portion of lead 16 intra-pericardially via a percutaneous subxiphoid approach. In some examples, the tools and implant techniques described herein could be used for implanting other medical devices or components thereof and/or for other spaces within the patient, such as, implanting a leadless pacemaker on or near outside of heart via substernal access.

Figure 2:
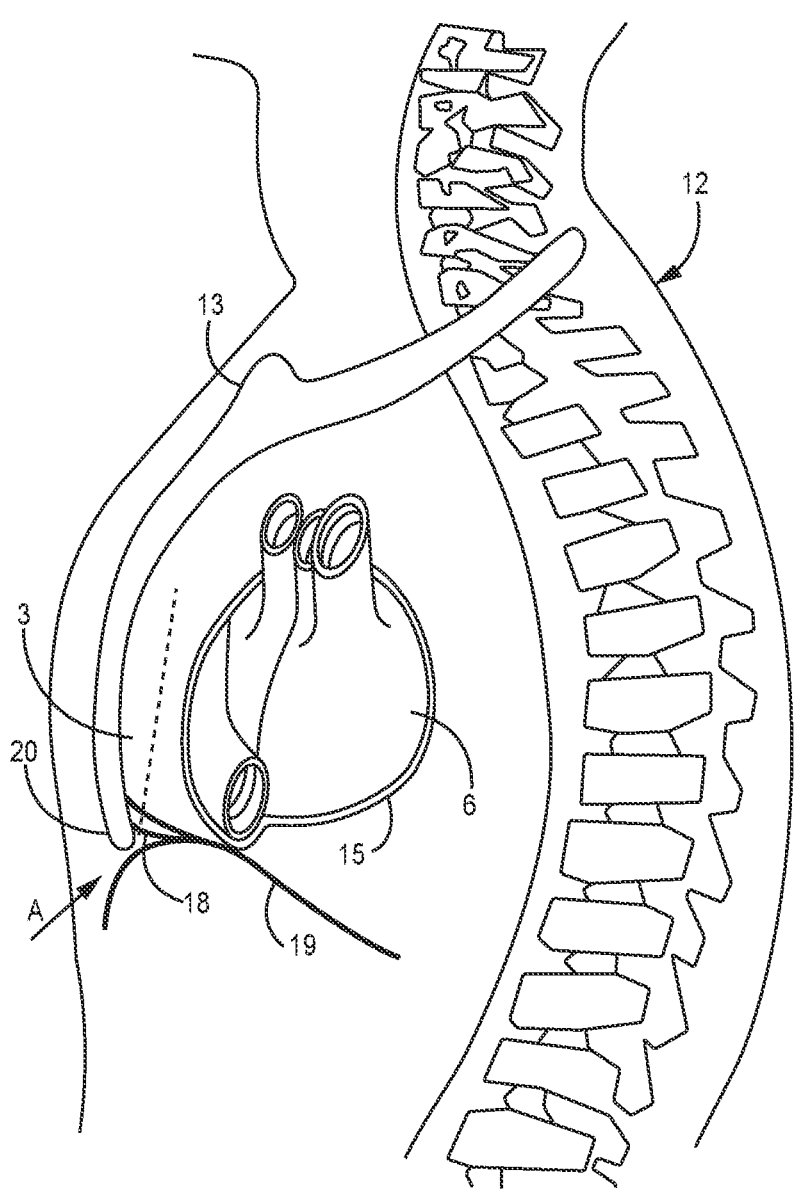
FIG. 2 is a schematic for describing sub-sternal access.

FIG. 2 is a schematic showing an access site A for making a passageway between a patient's diaphragm 19 and xiphoid process 20 of sternum 13, for example, to create a sub-sternal tunnel in which to position a medical device, such as medical electrical lead 16. After making a superficial incision, an operator, using a suitable tunneling tool, may open a passageway between diaphragmatic attachments 18 and diaphragm 19, for example, by blunt and/or sharp dissection, in which the operator may employ a tunneling tool, such as those example tools described herein, to both create the passageway and then form a sub-sternal tunnel (e.g. along the dotted line of FIG. 2). Because the bony structure of the sternum inhibits external palpation, the operator must take extra care, during the dissection (e.g., blunt and/or sharp) and/or tunneling, not to injure sub-sternal structures or the chest cavity, which could compromise the pleura of the lungs or the heart 6. Tools and associated methods disclosed herein are configured to help an operator gain the desired sub-sternal access and create a space in which to position a medical device, such as medical electrical lead 16, in a controlled fashion that mitigates the risk of injuring bodily organs.

In some examples, a distal portion of lead 16 may be implanted to be located between the posterior sternum 13 and the anterior wall of the heart 6. The implant procedure may be performed by using a blunt trocar with a flexible port to create a small tunnel near the posterior aspect of the sternum 13 via entry into the body near the xiphoid process 20. The distal portion of lead 16, e.g., the portion of lead 16 carrying some or all of electrodes 22, 24, 26, 28, is then placed in the anterior mediastinum. The proximal end of lead 16 is then tunneled subcutaneously or submuscularly to a left midxillary location under and connected to the pulse generator 14. Pulse generator 14 and lead 16 are able to provide, e.g., defibrillation, anti-tachycardia pacing (ATP), bradycardia pacing, post-shock pacing, and asystole "lifeboat pacing."

Suitable tunneling tools with blunt trocars may be utilized to implant lead 16 in patient 12. However, patients that have had previous median sternotomies tend to have extensive scar tissue and the pericardium is often adhered to the posterior of the sternum. This scar tissue makes it very challenging and, in some cases, relatively undesirable for a blunt trocar to create a small tunnel in the anterior mediastinum. A surgeon may not want to enter the substernal space of such patients unless they have direct visualization of the location. Thus, patients that have had one or more previous median sternotomies may be less likely to receive an extravascular ICD or other medical device that includes the implantation of distal portion of lead 16 between the posterior sternum 13 and the anterior wall of the heart 6 in the manner described above.

In accordance with some examples of the disclosure, a tunneling tool (or trocar) is described that allows for a forward, hemispherical view and selective dissection (e.g., selective between blunt and sharp dissection) of tissue while tunneling through diaphragmatic attachments, pericardial adhesion, and other soft tissue. Examples include tunneling tools having a knife blade or other cutting tool with a sharp edge, e.g., on the distal end of the tool, for accessing the substernal space, dissection adhesions, and creating working room, e.g., in the thoracic cavity. Such tunneling tools may also include an optical window for a surgeon or other user to visualize, e.g., using an endoscope inserted within the tunneling tool, the movement of a distal end of the tunneling tool through tissue. Such visualization may provide for better guidance of the tunneling tool during an implant procedure and allow for a clinician to identify locations in which it may be desirable to deploy the cutting tool, e.g., to cut tissue adjacent the distal end of the tunneling tool using sharp dissection rather than blunt dissection.

Examples of the disclosure may provide tools that allow for blunt dissection/tunneling as well as transection of adhesions under direct visualization. Such a tool enables safe placing of extravascular ICDs even in patients with previous sternotomies. The optical window with integrated knife or other cutting blade may allow for easy identification of tissue prior to dissection during a tunneling procedure. Example of the disclosure may also allow for easier access into the thorax of a patient with previous sternotomies for a coronary artery bypass graft (CABG) or valve replacement. The example tool may allow for the reduction of pericardial adhesions to create working space for placement, adjustment, and removal of lead.

Figure 3:
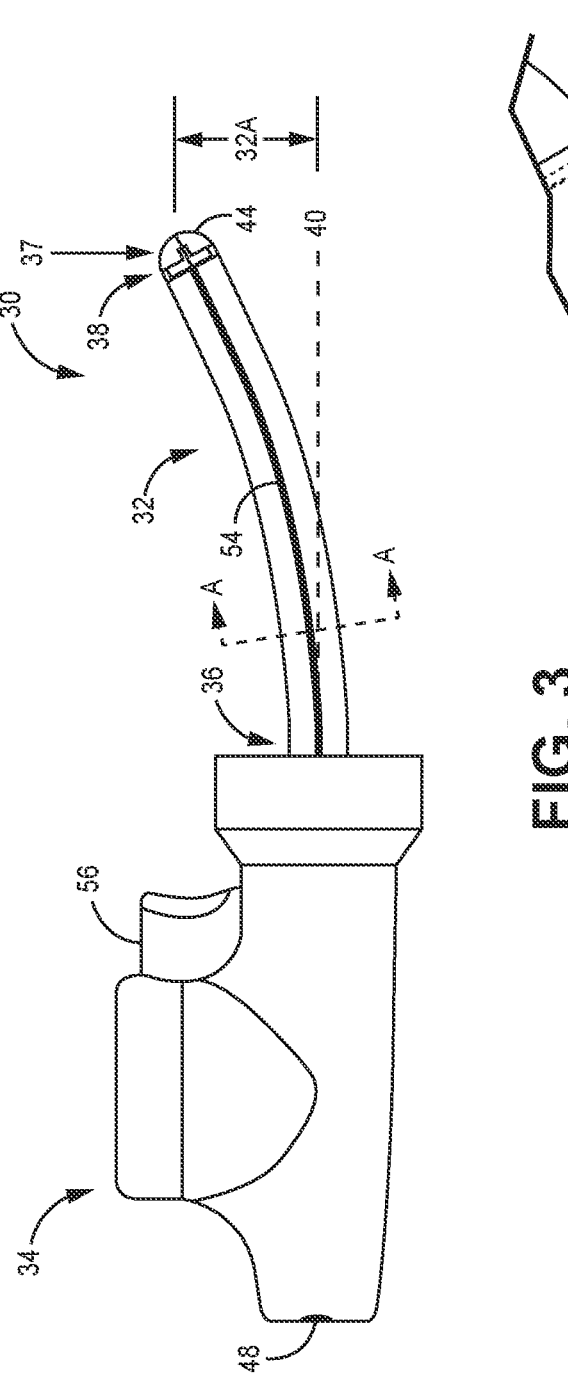
FIGS. 3-6 are schematic diagrams illustrating an example tunneling tool according to an example of the disclosure.
Figure 4:
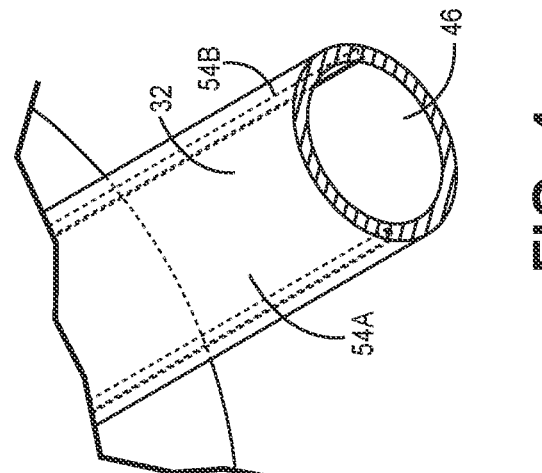
Figures 5A, 5B:
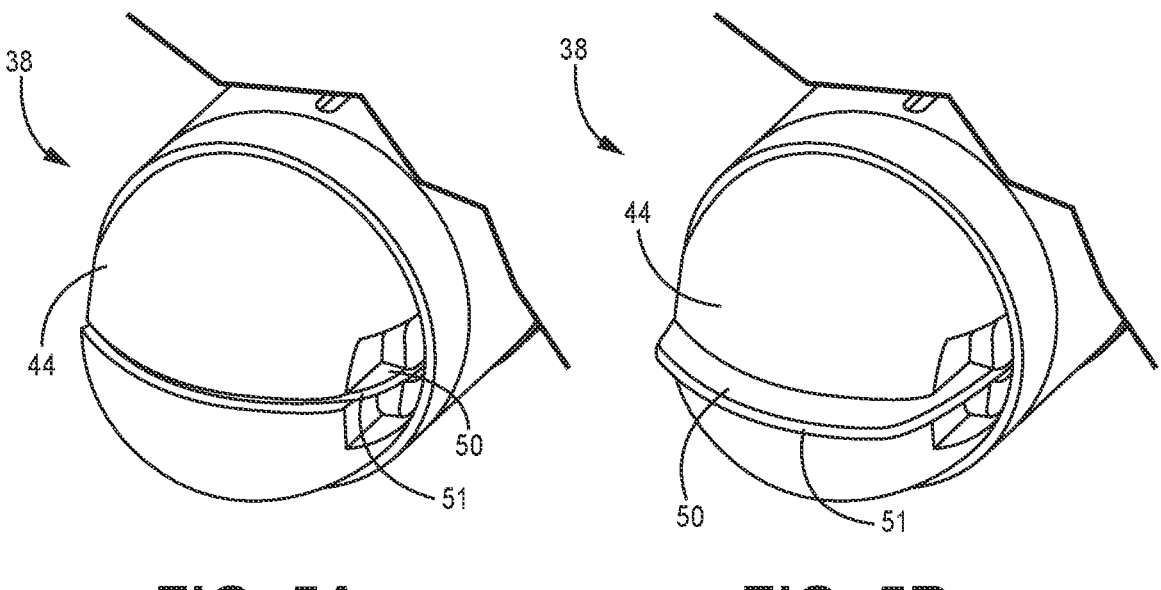
Figure 6:
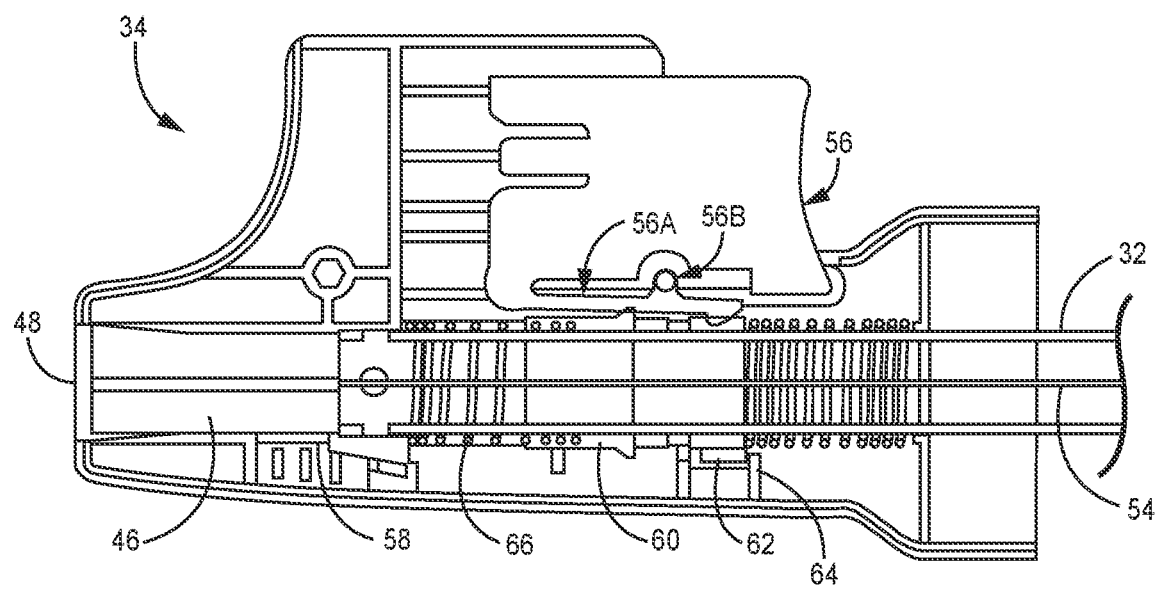

FIGS. 3-6 are functional schematic diagrams illustrating an example tunneling tool 30 for gaining sub-sternal access and creating a sub-sternal tunnel in a patient, according to some examples. FIG. 3 illustrates tunneling tool 30 including tunneling shaft 32 and handle 34. FIG. 4 illustrates a cross-section view of tunneling shaft 32 about cross-section A-A shown in FIG. 3. FIGS. 5A and 5B illustrate the distal end 38 of tunneling shaft 32. FIG. 6 illustrates a cross-sectional view of handle 34.

As shown in FIG. 3, tunneling shaft 32 of tunneling tool 30 extends from proximal end 36 to distal end 38 (or "distal tip 38"). Tool 30 also includes handle 34, which is shown coupled to proximal end 36 of tunneling shaft 32. Rather than extend from proximal end 36 to distal end 38 in a linear or straight manner, at least a portion of tunneling shaft 32 extends in a curved orientation from proximal end 36 to distal end 38, e.g., relative to axis 40. Axis 40 may be defined by a central longitudinal axis of handle 34 or may be defined by a portion of shaft 32 that extends initially from handle 34 in a substantially straight manner before exhibiting a curved orientation beginning at a point between proximal end 36 and distal end 38 of shaft 32. The curved orientation of tunneling shaft 32 results in offset 32A between distal end 38 and axis 40 shown in FIG. 3. Offset 32A may range from approximately 0.35 inches to approximately 1.25 inches, such as, approximately 0.720 inches, although other examples are contemplated. In some instances, the curvature of tunneling shaft 32 may maintain the path of the distal tip close to posterior side of sternum and away from vital organs like lung or heart during a tunneling procedure.

In some examples, tunneling shaft 32 be curved about the entire length from proximal end 36 to distal end 38 (e.g., as shown in FIG. 3) or may include one or more sections that are substantially straight with one or more other sections that are curved. For example, a proximately portion of the tunneling shaft 32 extending directly from handle 34 may be approximately straight for some of the length of tunneling shaft 32 and then transition to a more distal portion of tunneling shaft 32 that is curved. In some examples, the curved portion of tunneling shaft exhibits a radius of curvature of about 15 inches to about 40 inches.

Tunneling shaft 32 may be tubular, e.g., have a circular or oval outer profile and/or define one or more inner lumens, as shown in FIGS. 4-6. Any suitable material may be used for tunneling shaft 32, e.g., metals (stainless steel, coated steel, titanium alloys, aluminum alloys and others) and plastics (unfilled and filled with suitable fiber like glass or carbon for strength and rigidity) may be utilized. Suitable plastic materials include but are not limited to acetal copolymer, polytetrafluoroethylene (PTFE) (e.g., TEFLON), polyether ether ketone (PEEK), polyphenylsulfone (PPSU) (e.g., RADEL), and polycarbonate. In some examples, tunneling shaft 32 may be formed of a material that allows for all or at least a portion of tunneling shaft 32 to be transparent along the length of shaft 32. Shaft 32 may be substantially rigid so the clinician can control accurately the position of the tip in relation to vital organs under visualization afforded by fluoroscopy or other techniques via optical window 44. To that end, in some examples, the tip of shaft 32 preferably has at least some metal components (like a metal blade) which will allow visualization using suitable medical imaging technology.

In some examples, rigidity of shaft 32 may be described in the context of possible forces that may act of shaft 32, e.g., during an implant procedure. As one example, there may be a force an operator may apply to keep shaft 32 (e.g., distal end 38) pressed against sternum 13 of patient 12. The rigidity of shaft 32 may be such that shaft 32 does not flex significantly when the operator is biasing shaft 32 upwards/anteriorly. In some examples, shaft 32 exhibits substantially no flex when greater than about 5 pounds of force is applied to distal end 38 in direction 37 shown in FIG. 3. In some examples, shaft 32 does not "jam up" (e.g. can still deploy cutting tool 50 and/or allow for visualization via optical window 44) when greater than about 5 pounds of force is applied to distal end 38 in direction 37 shown in FIG. 3.

Another example force that may act on shaft 32 is a torque on shaft 32 when an operator is trying to keep shaft 32 aligned during insertion. If the operator is rotating shaft 32 back and forth along the axis 40, shaft 32 must have substantial rigidity to sweep back and forth on the posterior side of sternum 13, clear away adhesions, and still "fire" without jamming (e.g., still deploy cutting tool 50) on the order of about 5 inches*pound of torque.

Tunneling shaft 32 may exhibit any suitable shape and dimensions. While FIG. 4 shows that tunneling shaft 32 has a substantially circular cross-section, other example cross-section shapes are contemplated. For example, as described further below, in some examples, tunneling shaft 32 may exhibit an oval cross-section. The outer diameter (in the case of a circular cross-section) or greatest outer dimension (in the case of a non-circular cross-section) of tunneling shaft 32 may range from about 3 millimeters (mm) to about 15 mm, although other examples are contemplated. The length of tunneling shaft 32 from proximal end 36 directly adjacent handle 34 to proximal end 38 may range from about 4 inches to about 12 inches, although other examples are contemplated. In examples in which a portion of shaft 32 is substantially straight from the proximal end 36 adjacent to handle and then transitions to a curved portion at a point between proximal end 36 and distal end 38, approximately ⅓ (one-third) of the length of shaft 32 out of proximal end 36 may be approximately straight. In some examples, shaft 32 may have a portion that is approximately straight for a length of about 0.5 inches to about 1.5 inches (e.g., in the case of shaft 32 having an overall length of about 4 inches). In some examples, shaft 32 may have a portion that is approximately straight for a length of about 3 inches to about 5 inches (e.g., in the case of shaft 32 having an overall length of about 12 inches). In some examples, approximately ⅔ (two-thirds) of the overall length of shaft 32 out of proximal end 36 may be approximately straight. In some examples, shaft 32 may have a portion that is approximately straight for a length of about 7 inches to about 9 inches (e.g., in the case of shaft 32 having an overall length of about 12 inches).

Tunneling shaft 32 defines an inner lumen 46 that extends from the proximal end 36 to distal end 38. As shown in FIG. 6, inner lumen 46 runs from tunneling shaft 32 through handle 34, terminating at proximal opening 48 for handle. Distal end 38 of tunneling tool 32 also include optical window 44 that is shaped to allow for blunt dissection when tunneled through tissue of patient 12, e.g., using one or more of the techniques described herein. In the example of FIGS. 3-6, optical window 44 has a dome shape for the leading edge to allow for blunt dissection. However, other shapes are contemplated. Optical window 44 may be formed of a transparent material, for example glass, quartz or clear plastics like polycarbonate (e.g., LEXAN) or acrylic. During an implant procedure, an endoscope or other optical tool may be inserted into lumen 46 via proximal opening 48 in handle 34 and advanced through lumen 46 to distal end 38 of tunneling tool 32 adjacent optical window 44. In this manner, a surgeon or other user may visualize the path of distal end 38 when advanced through tissue of patient 12 during the insertion of tunnel tool 32 into patient 12.

Additionally, as shown in FIGS. 5A and 5B, tunneling tool 30 includes cutting tool 50 at distal end 38. Cutting tool 50 may take the form of a knife blade, scalpel blade, or other tool with a sharp edge 51 that is configured to cut through tissue, such as, scar tissue, of patient 12 while tool 30 is tunneled in the sub-sternal space 3 of patient 12 to a target location. Cutting tool 50 may be configured to be selectively actuated by a surgeon or other user from a recessed position (as shown in FIG. 5A) to a deployed position (as shown in FIG. 5B). When cutting tool 50 is in the recessed position, the lead or cutting edge of cutting tool 50 is recessed into distal end 38 of shaft such that the outer surface of optical window 44 defines the leading edge of the tool, allowing for blunt dissection of tissue while tunneling shaft 32 is advanced in sub-sternal space of tissue. Conversely, when cutting tool 50 is in the deployed position, cutting tool 50 defines the leading edge of the tunneling shaft 32, allowing for tissue, such as, scar tissue, to be cut by the tool by sharp dissection rather than be bluntly dissected.

Any suitable mechanism may be utilized to allow for cutting tool 50 to be transitioned between the recessed position (FIG. 5A) and deployed position (FIG. 5B). For example, as shown in FIGS. 3, 4, and 6, tunneling shaft 32 includes blade arms 54A and 54B (collectively "blade arms 54") parallel to the plane of leading edge 51 of cutting tool 50 within tunneling shaft 32, which are coupled to cutting tool 50 at the distal end and extend back to handle 34. Blade arms 54 may be located within tunneling shaft 32, inside inner lumen 46 and adjacent to the inner wall of tunneling shaft 32, and/or adjacent to the outer surface of tunneling shaft 32 (e.g., within tracks recessed into tunneling shaft 32). In the example in which blade arms 54 are located adjacent the outer surface of tunneling shaft 32 (e.g., within recessed tracks), tunneling tool 30 may include an outer sheath, e.g., a thin shrink wrap, that assists in securing blade arms in place relative to tunneling shaft 32.

Blade arms 54 are mechanically coupled to handle 34 such that the actuation of trigger 56 translates blade arms 54 along curved shaft 32 towards distal end 38 of tool 30 to transfer mechanical energy to cutting tool 50 to actuate cutting tool 50 from the recessed position to the deployed position. In the deployed position, sharp/leading edge 51 of cutting tool 50 may extend about 0.25 mm to about 2 mm beyond distal end 38 of tunneling shaft 32. Put another way, in the deployed position, sharp/leading edge 51 of cutting tool 50 may extend about 0.25 mm to about 2 mm beyond the leading edge of distal end 38, e.g., the outer surface of optical window 44, when cutting tool 50 is in the recessed position.

In some examples, the depression (pulling) of trigger 58 actuates cutting tool 50 from the recessed position to the deployed position and cutting tool 50 may remain in the deployed position until trigger 58 is released. Alternatively, tunneling member 30 may be configured such that the actuation of trigger 56, e.g., depression or depression and release of trigger 56, may result in cutting tool 50 being actuated from the recessed position to the deployed position and then automatically returned to the recessed position, e.g., after cutting tool 50 advances forward a pre-set distance. In some examples, a surgeon or other user may hold handle 34 of tool 30 stationary when trigger 56 is depressed to control the length of tissue that is dissected by cutting tool 50, which approximately corresponds to the length at which sharp/leading edge 51 of cutting tool 50 extends out of distal end 38 when trigger 56 is depressed to move cutting tool 50 into the deployed position. Alternatively, or additionally, a surgeon or other user may advance tunneling shaft 32 forward by handle 34 when cutting tool 50 is held in the deployed position, where the length of tissue dissection by cutting tool 50 corresponds generally to the length that tunneling shaft 32 is advanced under the control of the surgeon or other user.

As one example, in the configuration shown in FIG. 6, drive arms 54 are connected to a spring/hammer/bushing mechanism in handle 34 that includes scope retention slot 58, hammer 60, blade bushing 62 and bushing stop 64. When trigger 56 is pulled, hammer 60 is retracted against spring 66. The trigger 56 has a cantilever beam 56A with a hook. The hook engages the hammer 60 and drives it against spring 66. The beam 56A has also the post 56 B interacting with the slot in the wall of the handle body (not shown). When the trigger 56B is advanced sufficiently, the pin 56B, guided by the slot raises the hook and releases the hammer 60. Upon release, hammer 60 springs forward impacting blade bushing 60 to transmit mechanical energy to blade drive arms 54 until impacting a stop point defined by bushing hard stop 64. Bushing hard stop 64 in handle 34 prevents blade bushing 62 from advancing cutting tool 50 beyond a safe distance out of distal end 38 of tunneling shaft 32.

Figure 19:
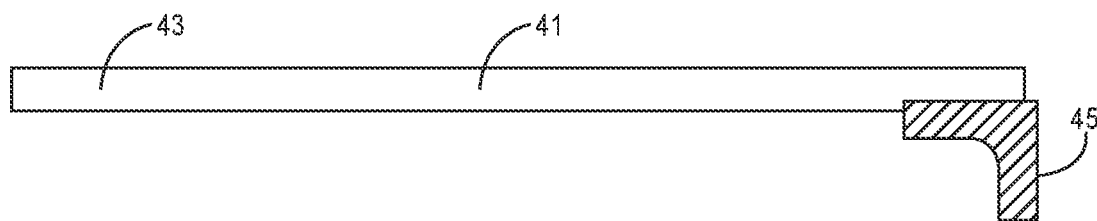
FIG. 19 is a conceptual drawing of an example introducer sheath that may be used in conjunction with, e.g., the tunneling tool of FIG. 3.

During a procedure to gain sub-sternal access and create a sub-sternal tunnel in a patient, e.g., to implant a medical device such as lead 16, tunneling shaft 32 may be inserted into the inner lumen of an introducer sheath, e.g., wherein the sheath is sized to extend from approximately distal end 38 to approximately proximal end 36 of tool shaft 32 prior to insertion and advancement of tunneling shaft 32 in patient 12. An example of an introducer sheath 41 is illustrated in FIG. 19. Sheath 41 includes a body 43 and a handle 45. Body 43 of sheath 41 defines an inner channel. In one example, sheath 41 may be an open sheath as illustrated and described in U.S. patent application Ser. No. 14/196,298 and U.S. patent application Ser. No. 14/196,443, both of which are incorporated herein by reference in their entireties. In the case of an open sheath, sheath 41 may include an opening along the length of body 43 and the inner channel is accessible via the opening anywhere along the length of body 43. In another example, sheath 41 may be a splittable sheath in which body 43 includes a score or other weakened portion to permit splitting of body 43, e.g., as illustrated and described in further detail in U.S. patent application Ser. No. 14/196,443, previously incorporated above. In yet another example, sheath 41 may be a sheath without any gap or score on body 43, in which case sheath 41 may be removed by slitting the sheath using a slitter, as illustrated and described U.S. patent application Ser. No. 14/196,443, previously incorporated above. Sheath 41 may have other properties describe above in reference to U.S. patent application Ser. No. 14/196,298 and U.S. patent application Ser. No. 14/196, 443 or any commercially available sheaths.

The distal portion of the introducer sheath 41 may have an open end so as to no obstruct the view through optical window 44 and deployment of cutting tool 50 at distal end 38 of tunneling shaft 32. Also, the open end allows for insertion of a lead to the targeted area. Once tunneling shaft 32 is inserted into the introducer sheath 41, distal end 38 may be inserted into an incision site, e.g., at access site A, and then tunneled superiorly to both create the passageway and then form a sub-sternal tunnel (e.g. along the dotted line of FIG. 2). During the tunneling, a surgeon or other operator may control the advancement and direction of tunneling shaft 32 by gripping handle 34, which is located external to the body of patient. The surgeon or other operator may view the path of distal end 38 of tunneling shaft 32 during the procedure through optical window 44 using an endoscope or other viewing device inserted within inner lumen 46 of shaft 32. The surgeon or other operator may tunnel through tissue of patient 12 by way of blunt dissection using distal end 38 of tunneling shaft with cutting tool in the recessed position. The surgeon or other operator may also selectively deploy cutting tool 50, e.g., to cut scar tissue or other areas where blunt dissection (e.g., via the distal end 38 when cutting tool 50 is recessed) does not allow for tunneling of tool shaft 32. Then, for example, tunneling shaft 32 of tool 30 is withdrawn from the patient's body, leaving the introducer sheath 41 within the sub-sternal tunnel. The operator may pass a medical device, such as the above described lead 16, through the sheath lumen, via a proximal opening of the introducer sheath. The surgeon or other operator may then remove the introducer sheath 41 from the body, leaving lead 16 within the sub-sternal tunnel, and then remove the sheath from the lead for example, by slitting or splitting the introducer sheath from around lead, according to some embodiments and methods.

FIGS. 18A-18D are conceptual diagrams illustrating a progression of tunneling tool 30 during an example tunneling technique in accordance with the disclosure to insert at least a portion of shaft 32 into the substernal space under sternum 13. As described herein, the surgeon or other operator may selectively deploy or recess cutting tool 50 at distal end 38 of tunneling shaft 32 as desired during the tunneling procedure as well as visualize the tissue space through optical window 44 during the procedure.

Figures 18A, 18B:
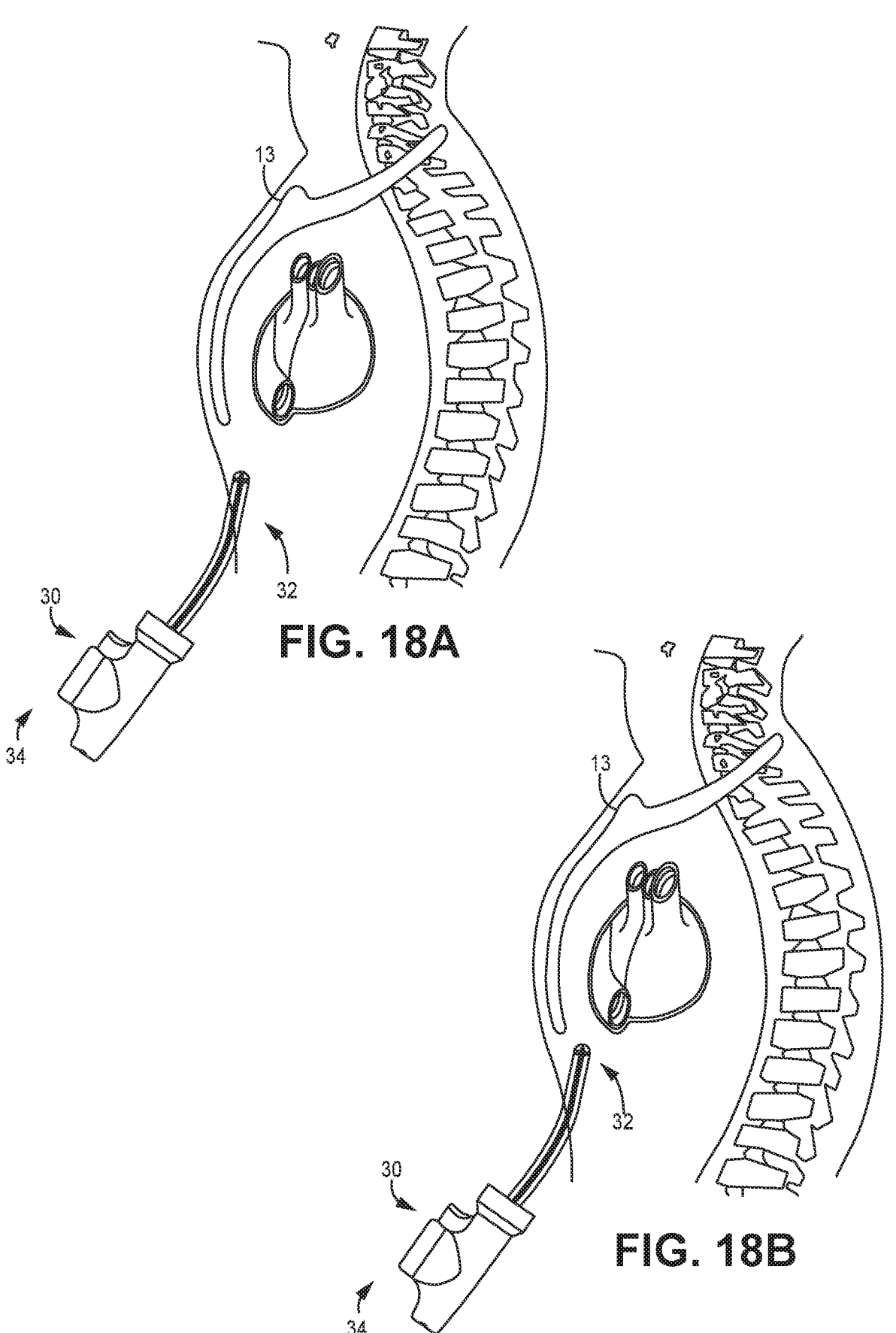
FIGS. 18A-18D is a is a schematic depicting the tool of FIG. 3, according to some example, being advanced superiorly beneath a sternum of the patient.
Figures 18C, 18D:
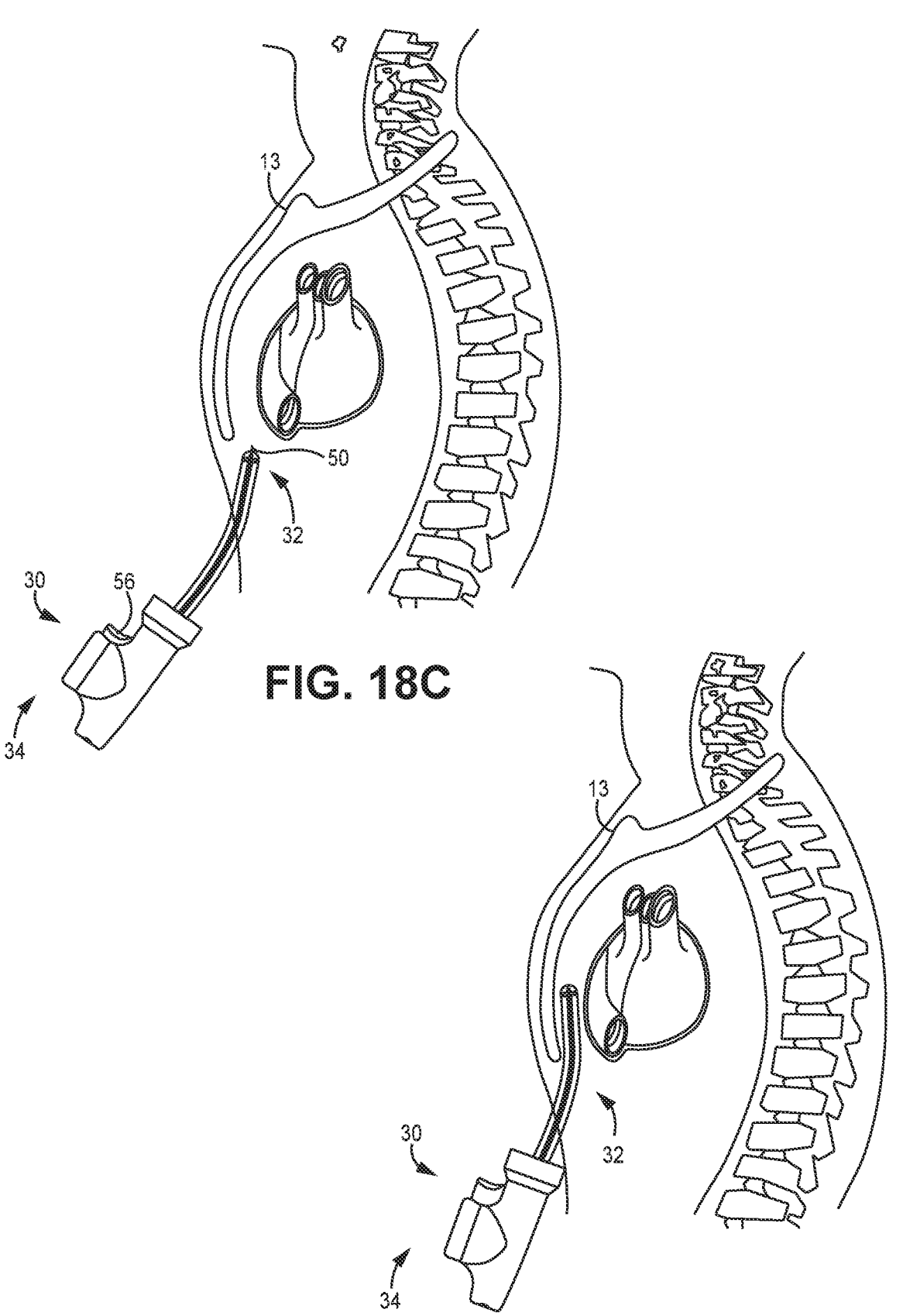

As shown in FIG. 18A, a distal portion of tunneling shaft is inserted through an incision site, e.g., at access site A shown in FIG. 2, with cutting tool 50 in the recessed position at distal end 38 of tunneling shaft 32, with the operator controlling the movement of shaft 32 by gripping handle 34, which is located externally. Handle 34 remains outside patient 12 to allow for a surgeon or other operator to maneuver tunneling shaft 32 along the desired path within the substernal space of patient 12. Distal end 38 of shaft 32 may be advanced superiorly, e.g., to the position shown in FIG. 18B, to create a portion of a passageway and a sub-sternal tunnel. The surgeon or other operator may view the path of distal end 38 of tunneling shaft 32 during the procedure through optical window 44 using an endoscope or other viewing device inserted within inner lumen 46 of shaft 32. The surgeon or other operator may tunnel through tissue of patient 12 by way of blunt dissection using distal end 38 of tunneling shaft with cutting tool 50 in the recessed position.

At the position shown in FIG. 18B, an operator may determine that a tissue (e.g., a diaphragmatic attachment, pericardium, scar tissue, or connective tissue) is directly adjacent to distal end 38 of shaft 32, e.g., using optical window 44. At that position, the operator may deploy cutting tool 50 to the deployed position (e.g., as show in FIG. 18C) to cut the tissue adjacent to distal end 38 of shaft 32, e.g., via sharp dissection with the leading edge 51 of cutting tool 50. The operator may deploy cutting tool 50 to the deployed position by depressing trigger 56. In some example, during the depression of trigger 56, the operator may hold the handle and, thus, shaft 32 generally in place while the cutting tool 51 is advanced out to distal end 38 to the deployed position to cut the adjacent tissue. Once the tissue has been cut by the deployment of cutting tool 50, cutting tool 50 may be retracted back to the recessed position (e.g., automatically or with the release to trigger 56) and then advanced by the operator past the cut tissue to the position shown in FIG. 18D, e.g., to provide a path for the placement of lead 16 in the anterior mediastinum.

As illustrated by FIGS. 18A-18D, an operator may tunnel or otherwise advance a distal portion of shaft 32 from the incision site to a desired location such that cutting tool 50 is selectively deployed from the recessed to deployed position, e.g., as needed cut through tissue such as, e.g., diaphragmatic attachment, pericardium, scar tissue, or connective tissue, adjacent to distal end 38 during the tunneling procedure. Depending on patient anatomy, there may be tissue in the anterior mediastinum or other anatomical location along the pathway of shaft 32. During initial insertion, shaft 32 may penetrate through diaphragmatic attachments that were not dissected with the initial incision. If a patient has not had a previous sternotomy or other procedure, the mediastinal tissue (pericardium, lungs) may move be moving freely. Open space may exist after creating the incision and air is introduced, but expansion of the lungs during breathing may fill this space. Tool 30 may be particularly useful for patients who have had a previous sternotomy or other open chest procedure. These patients may have severe adhesions to the posterior sternum as result. In such cases, the tissue may be a mixture of pericardium, scar tissue, or connective tissue that forms in response to the injury from the first surgery. When the distal portion of shaft 32 is introduced into these patients, shaft 32 may be tunneling and cutting (e.g., via selective deployment of cutting tool 50) through this mixture of tissue in order to safely place a lead, such as lead 16, as desired within patient 12 using the example techniques described herein.

As shown in FIGS. 18A-18D, the curvature of tunneling shaft 18 is such that the distal portion of tunneling shaft is biased towards in the inner surface of sternum 13. Additionally, the leading edge 51 of cutting tool 50 (illustrated in FIG. 5B, e.g.) extends along a plane that is nonorthogonal (e.g., generally parallel) to the plane of sternum 13 and outer surface of pericardial sac adjacent tunneling shaft 32. Such a configuration may allow for blade arms 54 to be driven from a mechanism within handle 34 more easily, e.g., compared to a configuration in which leading edge 51 of cutting tool 50 is rotated 90 degrees from that shown in FIG. 3.

Cutting tool 50 may have any suitable orientation when employed by tunneling tool 30. In the example of FIGS. 3-6, the plane of leading/sharp edge 51 of cutting tool 50 is oriented approximately parallel to the central longitudinal axis of handle 34 and direction in which trigger 56 is depressed to deploy cutting tool 50. Additionally, cutting tool 50 extends along a plane such that, during normal use tunneling through tissue in sub-sternal space 3 as described herein, cutting tool 50 is oriented non-orthogonal (e.g., approximately parallel) to the sternum inner surface, pericardium, and/or heart of patient 12.

In addition to or as an alternative to cutting tool 50, tool 30 may include an electrosurgery implement. In such an example, drive arms 54 may be configured to conduct current and insulated from tissue contact within tunneling shaft 32 when in a recessed position. An electrical connector may be located, e.g., be included in handle 34. In such an example, depressing trigger 56 may advance the electrosurgical tool out of distal end 38 temporarily to cauterize or dissect tissue.

Figure 7C:
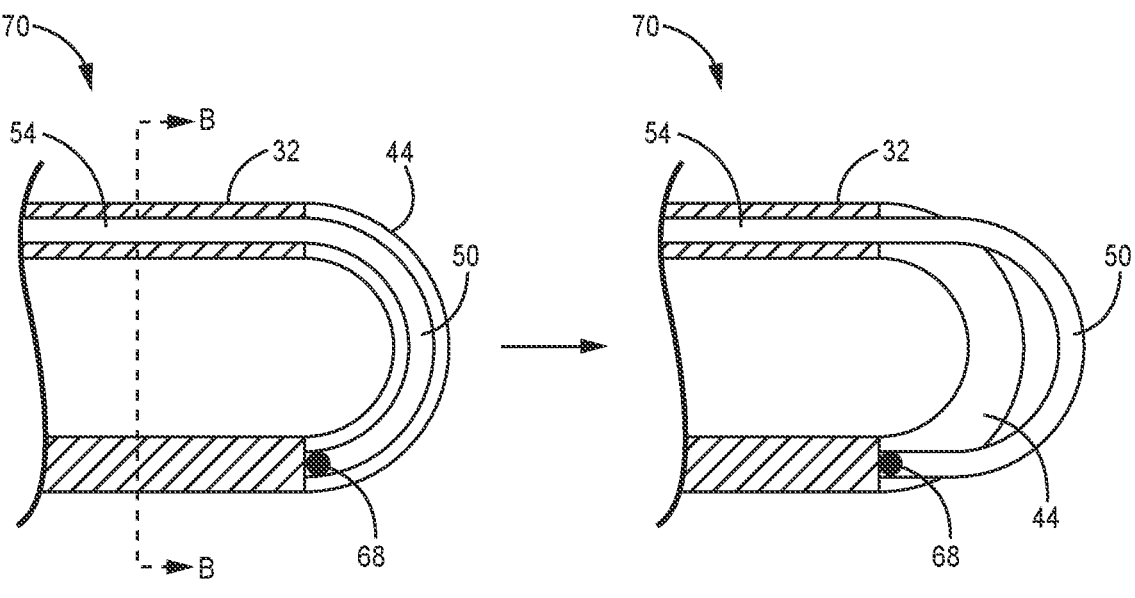
Figure 7C:
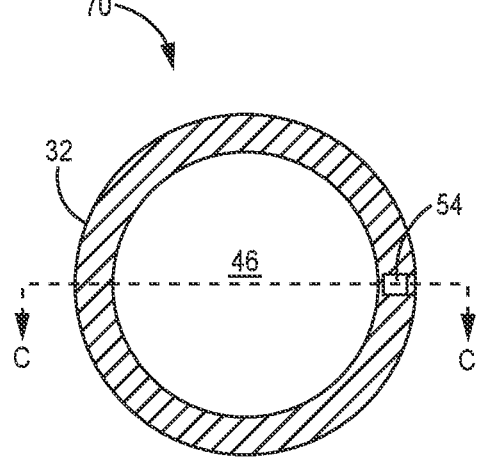

FIGS. 7A-7C are schematic diagrams illustrating the distal portion of another example tunneling tool 70 according to an example of the disclosure. FIGS. 7A and 7B illustrates a cross-sectional view of tunneling tool 70 taken along cross-section C-C of FIG. 7C. FIG. 7C illustrates a cross-sectional view of tunneling tool 70 taken along cross-section B-B of FIG. 7A. Tunneling tool 70 may be substantially the same as tunneling tool 30 described with regard to FIGS. 3-6, and similar features are similarly numbered. However, unlike tunneling tool 30, tool 70 includes a single blade arm 54 that translates to transmit mechanical energy from handle 34 to cutting tool 50 rather than two blade arms 54A, 54B as shown for tunneling tool 30. Single blade arm 54 may extend from handle 34 along curved tunneling shaft to cutting tool 50 located at distal end 38 of tunneling tool 70. As described previously, blade arm 54 may be translated (e.g., by depressing trigger 56) to move cutting tool 50 from a recessed position (as shown in FIG. 7A) to a deployed position (FIG. 7B). As illustrated, single drive arm 54 transmits mechanical energy from handle 34 to an adjacent side of cutting tool 50 while the other side of cutting tool 50 is anchored (e.g., via a pin) to a portion of tunneling shaft 32, such as, optical window 44. The transmitted energy causes cutting tool 50 to rotate about the anchoring point to expose the sharp leading edge of cutting tool 50 to tissue adjacent optical window 44. In some examples, the use of a single blade arm 54 instead of two or more blade arms, such as blade arms 54A and 54B of tunneling tool 30, allows for a reduced diameter of tunneling shaft 32.

Figure 8A:
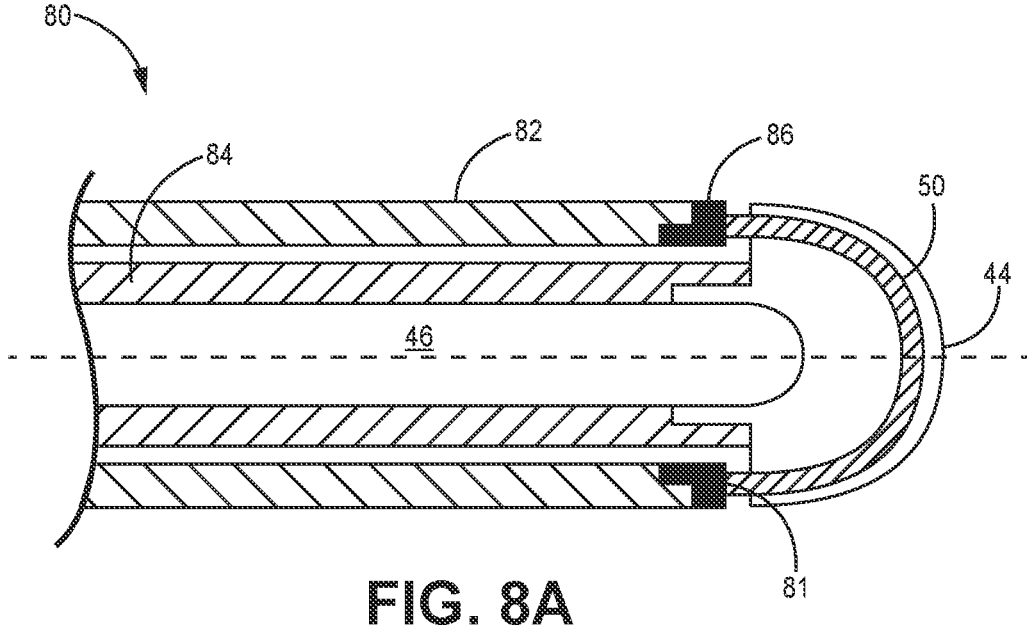
FIGS. 8A and 8B are schematic diagrams illustrating the distal portion of another example tunneling tool according to an example of the disclosure.
Figure 8B:
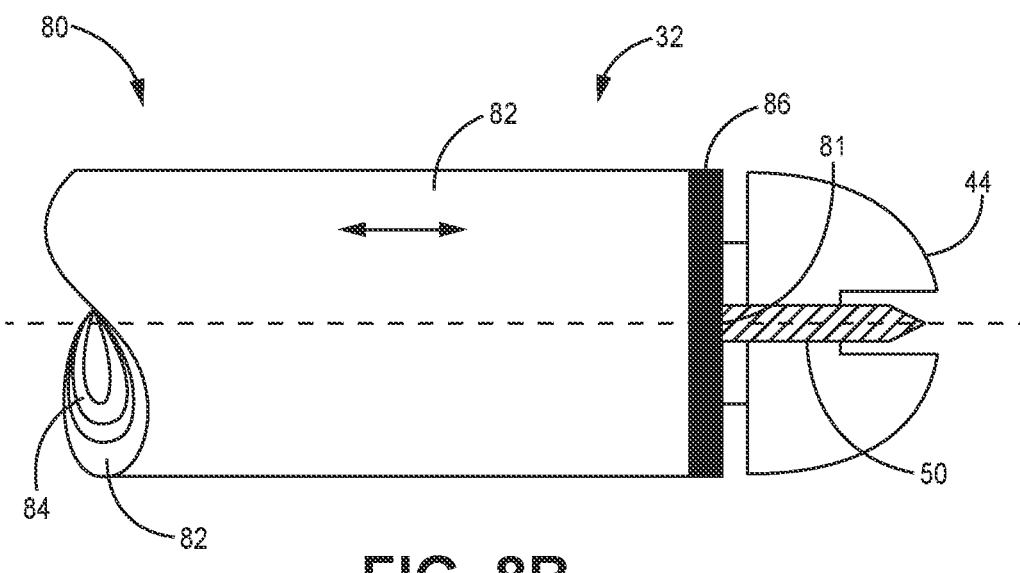

FIGS. 8A and 8B are schematic diagrams illustrating the distal portion of another example tunneling tool 80 according to another example of the disclosure. FIG. 8A is a cross-sectional view of cutting tool 70 from a perspective similar to that shown in the example of FIGS. 7A and 7B, and FIG. 8B is a side view of the distal portion of tunneling tool 80. Tunneling tool 70 may be substantially the same as tunneling tool 30 described with regard to FIGS. 3-6, and similar features are similarly numbered. However, rather than tunneling shaft 32 including a single curved tube within inner lumen, tunneling tool 80 includes a tunneling shaft 32 including a first curved tube 82 and second curved tube 84 of generally matching curvature. First tube 82 has a greater diameter than that of the diameter of second tube 84 such that second tube 84 is nested, e.g., coaxially, within first tube 82. First tube 82 and second tube 84 may be sized and configured to be moveable relative each other. In some examples, second tube 84 may be substantially rigid and made from, e.g., a metal or metal alloy, while first tube 82 may be constructed to be flexible, e.g., using a flexible plastic material.

In some examples, the movement of first tube 82 relative to second tube 84 may be actuated by depression of trigger 56 to selectively transition cutting tool 50 between a recessed and deployed configuration, e.g., similar to that described above with regard to tunneling tool 30 of FIGS. 3-6. However, rather than employing blade drive arms 54 to transfer the force from handle 34 to transition cutting tool 50 from a recessed to deployed position, in the example of FIGS. 8A and 8B, actuation of trigger 56 may move first tube 82 distally while second tube 84 remains stationary. Optical window 44 may be connected to stationary second tube 84. As shown in FIG. 8A, cutting tool 50 may be welded or otherwise connected to metal base 86 at location 81 at the distal end of first tube 82 such that the distal movement of first tube 82 actuates cutting tool 50 to extend out of the aperture in optical window 44 (shown in FIG. 8B) from a recessed to deployed configuration, e.g., to dissect tissue directly adjacent optical window 44. In other examples, second tube 84 is moveable with the actuation of trigger 56 while first tube 82 is stationary, where the cutting tool 50 is connected to second tube 84 and optical window 44 is connected to first tube 82. In such examples, the movement of second tube 84 may transition cutting tool 50 from a recessed to deployed configuration using trigger 56.

In some example, tunneling tool 80 may include a lubricious layer located between the outer surface of second tube 84 and inner surface of first tube 82 to promote movement of tubes 82 and 84 relative to each other. For example, the outer surface of the second curved tube 84 to be hard coated with lubricious layer 81, e.g., in the form of baked Teflon or other lubricant. Additionally or alternatively, lubricious layer 81 may be formed on the inner portion of first curved tube 82.

In some examples, both first tube 82 and second tube 84 may be flexible. In such examples, one or both of first tube 82 and second tube 84 (e.g., only second tube 84) may include one or more bendable wires (not shown) along a longitudinal length that may be malleable to allow for tunneling shaft to retain a curvature when bent by a user. For example, the bendable wire(s) may be embedded in the walls of first tube 82 and/or second tube 84, or otherwise coupled to first tube 82 and/or second tube 84 (e.g., using a heat shrinkable outer sheath). In this manner, the curvature or other shape of shaft 32 may be modified as desired by an operator to optimize the geometry of shaft 32 to the anatomy of a particular patient. In some examples, first tube 82 and/or second tube 84 may be extruded with a such a bendable wire, e.g., within the side wall of the tube. In some examples, the bendable wire(s) may be a gage 21 (about 0.0318 inch diameter) 301 stainless steel, ¼ hard wire although other examples are contemplated.

Like that of tunneling tool 30, tunneling tool 80 includes optical window 44 through which an endoscope or other optical device may employed to allow a surgeon or other user to visualize the space outside of distal end 38 of tool 80 during an implant procedure. Likewise, as described above, tunneling tool 80 includes a semi-circular cutting tool 50 (e.g., a semi-circular blade) that may be selectively actuated between a recessed and deployed position, e.g., to allow for tunneling tool 80 to be used for blunt and sharp dissection of tissue, respectively, during implantation in the sub-sternal space 3 as desired based on the tissue viewable via optical window 44. In some examples, semi-circular blade 50 is welded or otherwise attached in a perpendicular arrangement relative to a circular metal base 86.

Figure 9A:
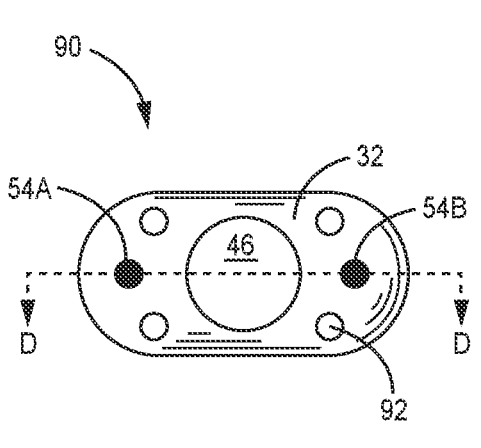
FIGS. 9A and 9B are schematic diagrams illustrating the distal portion of another example tunneling tool according to an example of the disclosure.
Figure 9B:
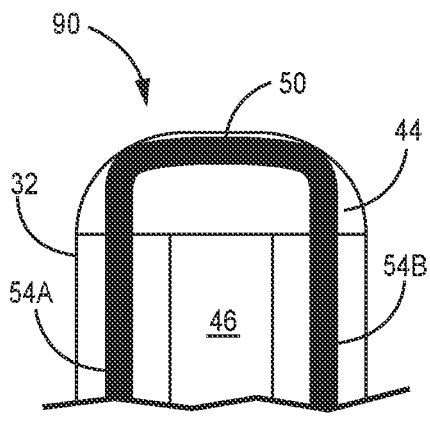

FIGS. 9A and 9B are schematic diagrams illustrating the distal portion of another example tunneling tool 90 from a side and top cross-sectional view according to another example of the disclosure. FIG. 9B is an illustration of cross-section D-D of tool 90 in FIG. 9A. Tunneling tool 90 may be substantially the same as tunneling tool 30 described with regard to FIGS. 3-6, and similar features are similarly numbered.

In the example of FIGS. 9A and 9B, tunneling shaft 32 has a substantially oval (e.g., elongated oval) cross-section in a plane orthogonal to the longitudinal axis of tool 90. The oval cross-sectional shape allows for substantially flat surfaces ("top" and "bottom" surfaces in the orientation shown in FIG. 9A) of tunneling shaft 32 to be adjacent to the sternum inner surface and pericardial sac outer surface when utilized according to the tunneling techniques described herein (as opposed to the rounded top and bottom surfaces of tool 30 shown in FIGS. 3-6). In some example, the "flat upper" surface of shaft 32 may be guided or otherwise in contact with sternum inner surface during a tunneling procedure, which may provide for increase stability of tool 90 in the hand(s) of a surgeon or other operator. Tunneling shaft 32 includes inner lumen 46, blade arms 54, and one or more additional lumen 92 (only a single lumen is numbered in FIG. 9) extending from proximal end 36 to distal end 38 of tunneling shaft 32.

In some examples, tunneling shaft 32 may be an extruded tube including the desired number of inner lumen with the desired size, e.g., diameter. The inner lumen(s) of tunneling shaft 32 be used for insertion of one or more scopes (e.g., a flexible endoscope) for visualization out of optics window 44, lead insertion/placement (e.g., in lieu of using an introducer sheath), blade drives arm(s) 54, bendable wire(s) for positioning and defining the curvature of tunneling shaft 32, stiffening rods, working channels for additional instruments (tools for contrast dyes, electrocautery), and the like. Like the other examples described herein, tunneling shaft 32 includes optical window 44 at distal end 38 to allow a surgeon to visualize the space adjacent to distal end 38 during a tunneling procedure as well as cutting blade 50 that may be selectively deployed and retract as need to cut tissue during the tunneling procedure. In the example of FIGS. 9A and 9B, the lead edge of cutting tool 50 extends in line with the long axis of the oval cross-section of tunneling shaft 32.

Figure 10A:
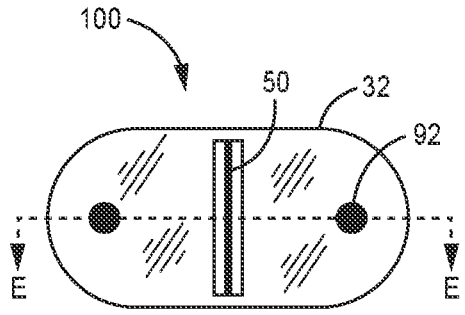
FIGS. 10A-10C are schematic diagrams illustrating the distal portion of another example tunneling tool according to an example of the disclosure.
Figure 10B:
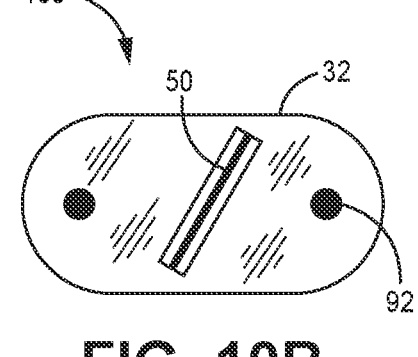
Figure 10C:
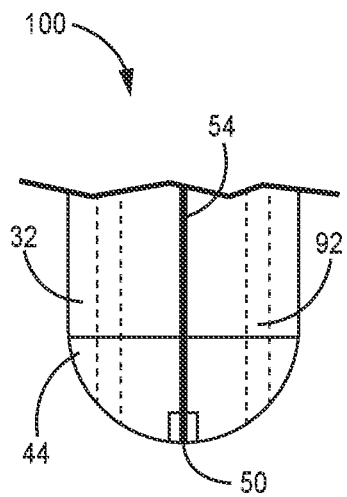

FIGS. 10A-10C are schematic diagrams illustrating the distal portion of another example tunneling tool 100 from a side (FIGS. 10A and 10B) and top cross-sectional view (FIG. 10C) according to another example of the disclosure. FIG. 10C is an illustration of cross-section E-E of tool 100 in FIG. 10A. Tunneling tool 100 may be substantially the same as tunneling tool 30 described with regard to FIGS. 3-6, and similar features are similarly numbered.

Like that of tool 90 of FIGS. 9A and 9B, tool 100 includes tunneling shaft 32 having a substantially oval cross-sectional shape. The oval cross-sectional shape allows for substantially flat surfaces (top and bottom surfaces in the orientation shown in FIG. 10A) of tunneling shaft 32 to be adjacent to the sternum inner surface and pericardial sac outer surface when utilized according to the tunneling techniques described herein (as opposed to the rounded top and bottom surfaces of tool 30 shown in FIGS. 3-6). As shown in FIGS.

10A and 10C, the leading edge of cutting tool 50 may extend in a direction substantially perpendicular to the long axis of the oval cross-section of tunneling shaft 32, and is located between additional (or "working") lumen 92. FIG. 10B illustrates an example in which the leading edge of cutting tool 50 may extend an angled, non-perpendicular direction relative to the long axis of the oval cross-section of tunneling shaft 32. The angled orientation of cutting tool 50 allows for the length of the cutting tool 50 to be longer than, e.g., the length of cutting tool 50 oriented perpendicular to the long axis of the oval cross-section, resulting in a larger cutting profile.

Figure 11A:
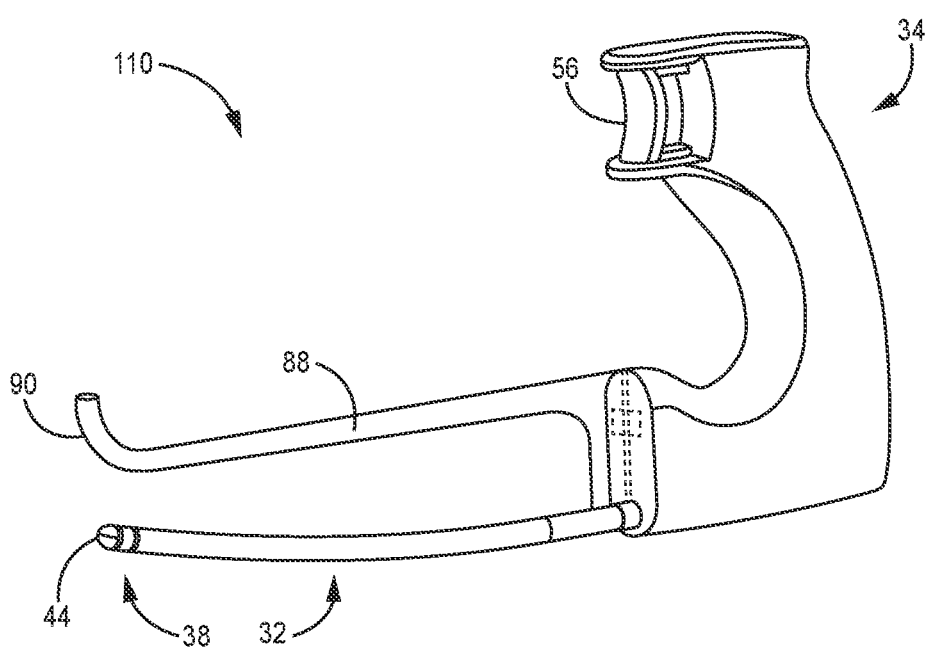
FIGS. 11A-11C are schematic diagrams illustrating another example tunneling tool according to an example of the disclosure.
Figure 11B:
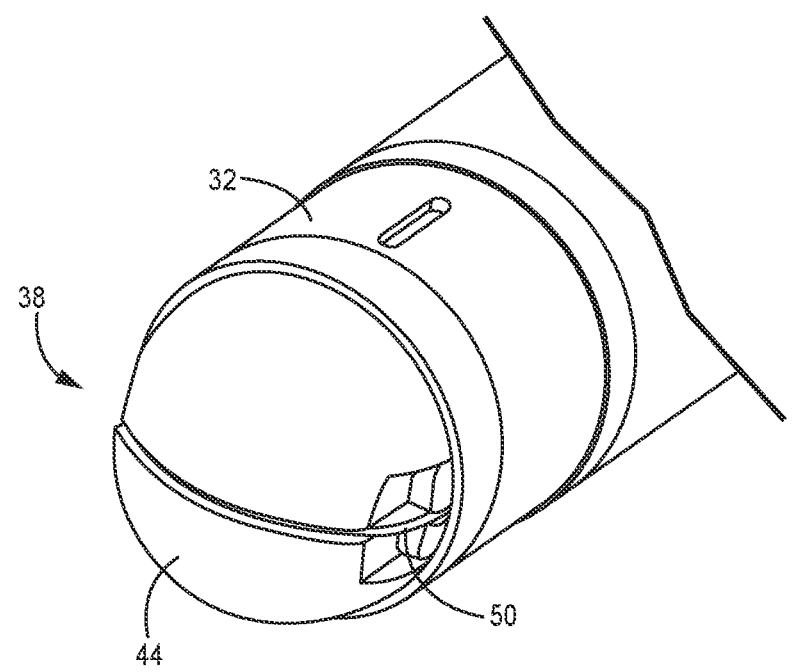
Figure 11C:
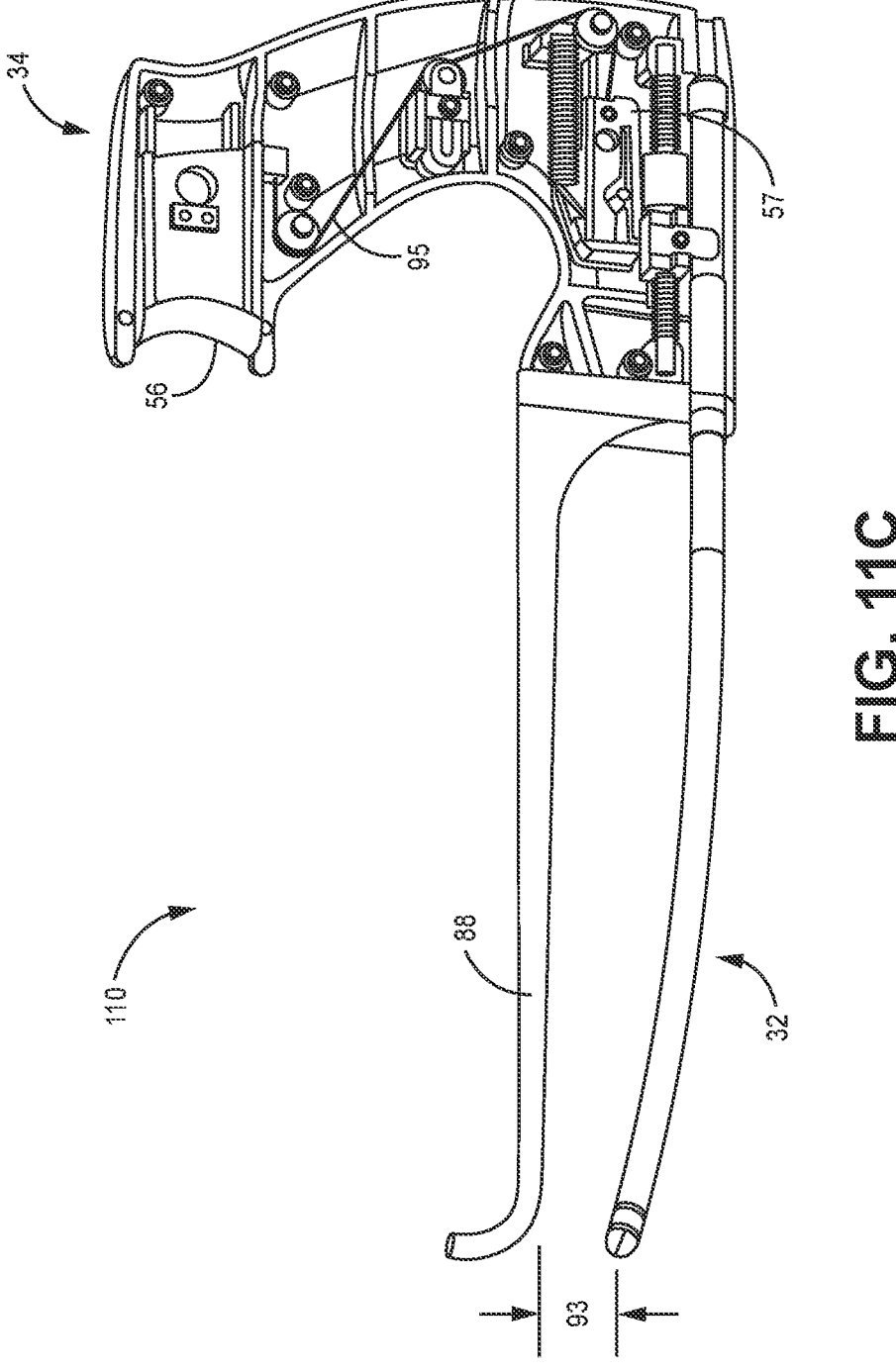

FIGS. 11A-11C are schematic diagrams illustrating another example tunneling tool 110 according to an example of the disclosure. Tunneling tool 110 may be substantially the same as tunneling tool 30 described with regard to FIGS. 3-6, and similar features are similarly numbered. FIG. 11B illustrates distal end 38 of tunneling shaft 32, which includes optical window 44 and cutting tool 50 (shown in the recessed position). FIG. 11C illustrates a view of tunneling tool 110 similar to that of FIG. 11A but with an outer portion of handle 34 removed to show, among others, the mechanism employed to allow trigger to be actuated such that mechanical energy is translated cutting tool 50, e.g., to selectively deploy cutting tool 50 for sharp dissection of tissue. Unlike that of tunneling tool 30, tool 110 includes guide member 88 extending from handle 34 adjacent to and coplanar with tunneling shaft 32. Tunneling shaft 32 is curved towards guide member 88. Handle 34 has a shape configured to receive fingers of a hand of a surgeon or other operator but may have any other suitable configuration for gripping. When gripped by the surgeon or other operator, a finger such as the index finger may be located in a manner that allows the finger to easily depress and release trigger 56.

During a procedure to gain sub-sternal access and create a sub-sternal tunnel in a patient, guide member 88 may help a surgeon or other operator in advancing tunneling shaft 32, once distal end 38 is inserted into patient 12. In some examples, curved distal portion 90 of guide member 88 may be configured to 'ride' on the skin over the sternum 13 without binding on the skin during such a procedure. In this manner, guide member 88 may limit the depth below the sternum 13 that tunneling shaft 32 may be advanced during the tunneling procedure. Further, the curvature of tunneling shaft 32 toward guide member 88 can cause distal end 38 to 'ride' adjacent an inside surface of sternum 13 during the superior advancement thereof as an additional aid to the operator. In some example, the distance 93 between guide member 88 and tunneling shaft 32 may be adjusted as desired by a surgeon or other operator, e.g., based on the physical characteristics of a patient. Examples of guide members 88 employed in a tunneling tool may include those described in U.S. patent application Ser. No. 15/204,579, by Malewicz et al., the entire content of which is incorporated herein by reference.

As shown in FIG. 11C, handle 34 includes an elastic member like a cable, chain or belt 95 that is coupled to trigger 56. When trigger is pulled, the elastic member drives the slider 57 which in turn activates the hammer mechanism deploying momentarily the cutting tool 50 to cut through adhesions. The cutting tool 50 retracts automatically as in the mechanism described above.

Figure 12:
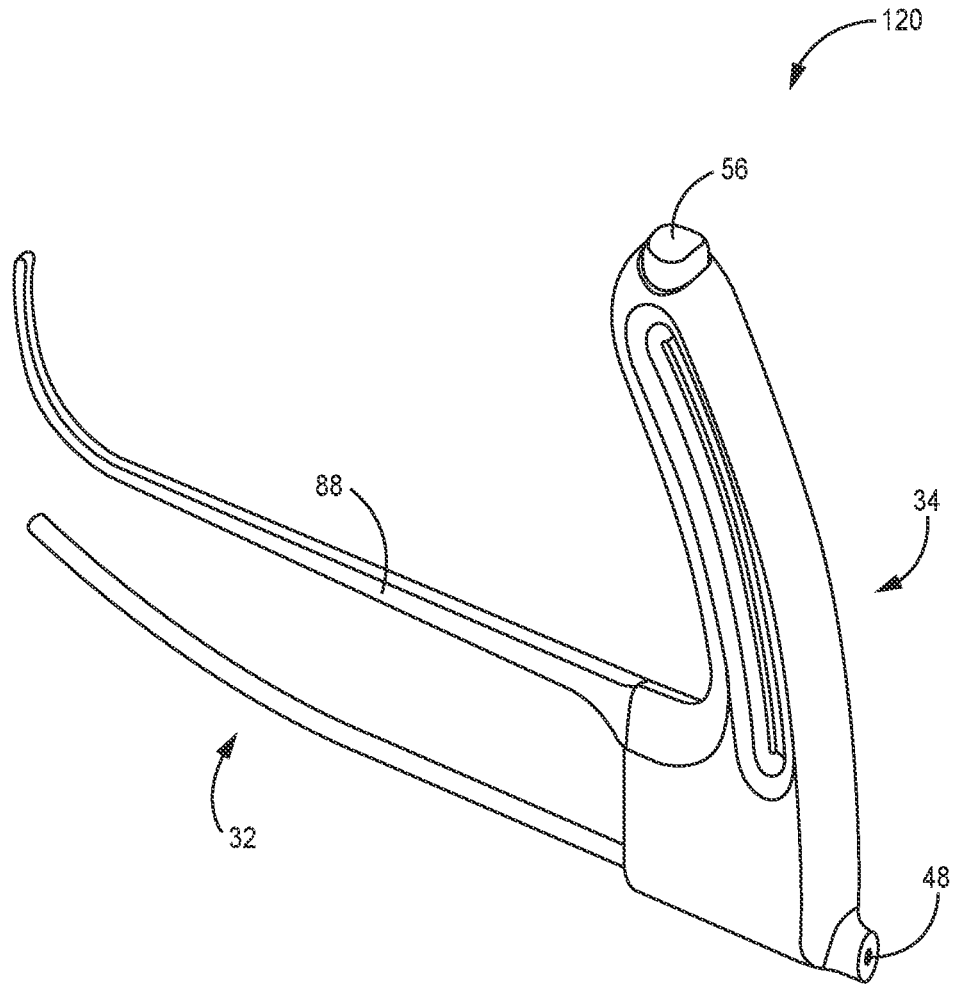
FIG. 12 is a schematic diagram illustrating another example tunneling tool according to an example of the disclosure.

FIG. 12 is a schematic diagram illustrating another example tunneling tool 120 according to an example of the disclosure. Tunneling tool 120 may be substantially the same as tunneling tool 110 described with regard to FIGS. 11A-11E, and similar features are similarly numbered. An endoscope or other tool be may be inserted into proximal opening 48 of handle 34 and advanced, e.g., through inner lumen 46 to or near distal end 38 of tunneling shaft 32. The shape of handle 34 of tool 120 is different from that of handle 34 of tool 110. For example, handle 34 is shaped such that when gripped by a hand of a surgeon or other operator, trigger 56 may be depressed or otherwise actuated by the thumb of that hand rather than a finger such as the index finger in the case of tool 110.

Figures 13A, 13B:
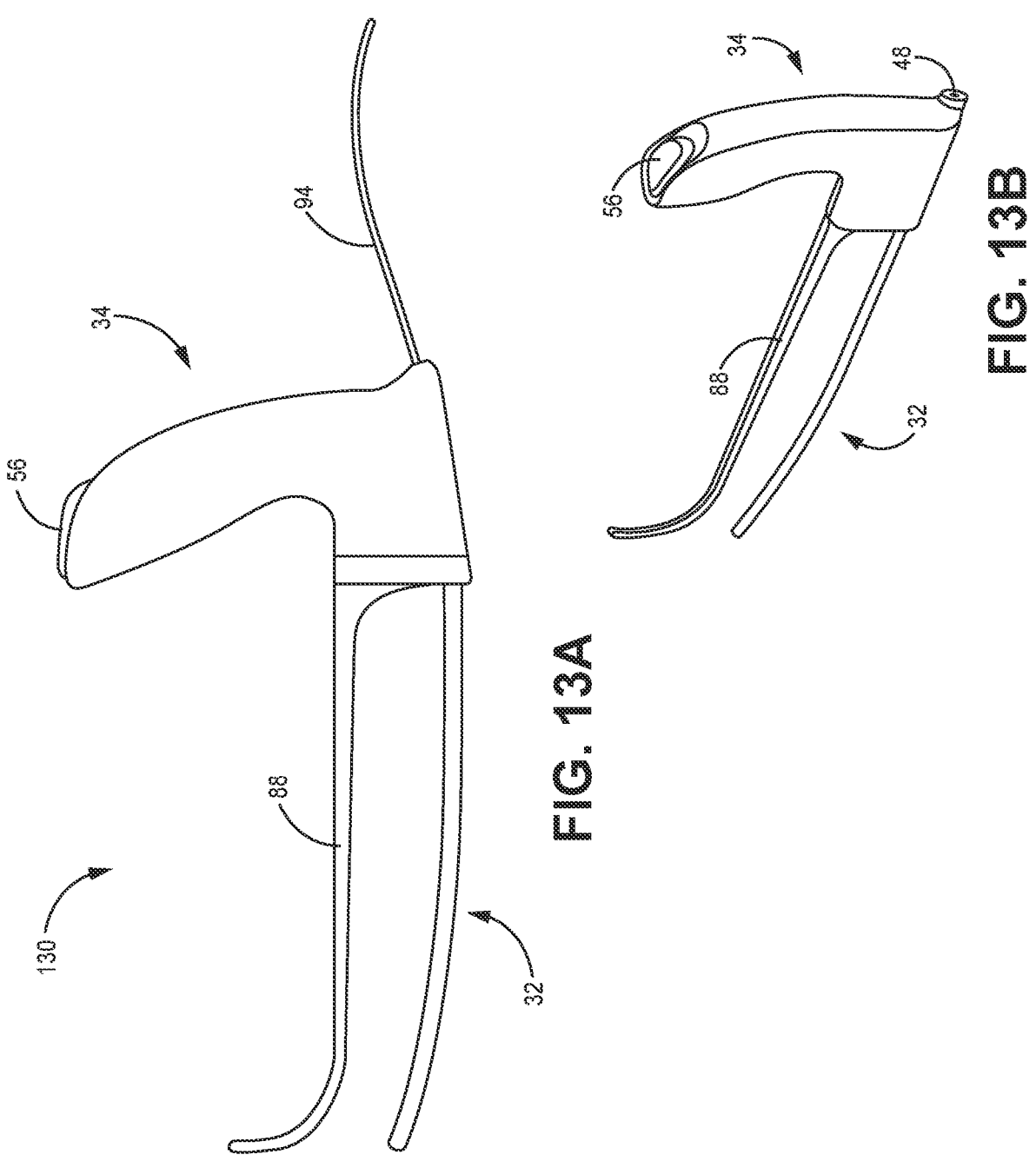
FIGS. 13A and 13B are schematic diagrams illustrating another example tunneling tool according to an example of the disclosure.

FIGS. 13A and 13B are schematic diagrams illustrating another example tunneling tool 130 according to an example of the disclosure. Tunneling tool 130 may be substantially the same as tunneling tool 120 described with regard to FIG. 12, and similar features are similarly numbered. FIG. 13B shows proximal opening 48 in handle 34 and FIG. 13A shows endoscope or another tool 94 inserted within proximately opening 48. As described previously, an endoscope or other tool 94 may be inserted into inner lumen 46 of tunneling shaft 32 via opening 48 in handle 34, e.g., to allow for visualization by a surgeon or other operator through optical window 44 at proximal end 38 of shaft 32 during a tunneling procedure. As shown in FIGS. 13A and 13B, trigger 56 may be shielded by adjacent walls of handle 34 by recessing trigger 56 to some extent into the surface of handle, e.g., to protect against unwanted depression of trigger 56 during a tunneling procedure.

Figure 14:
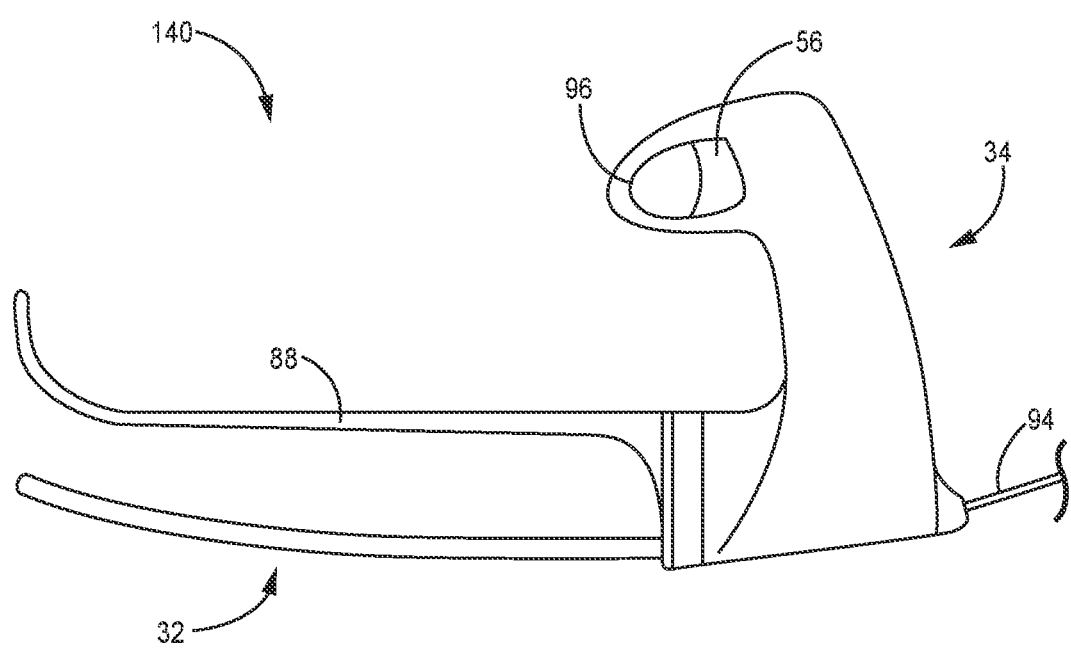
FIG. 14 is a schematic diagram illustrating another example tunneling tool according to an example of the disclosure.

FIG. 14 is a schematic diagram illustrating another example tunneling tool 140 according to an example of the disclosure. Tunneling tool 140 may be substantially the same as tunneling tool 110 described with regard to FIGS. 11A-11E, and similar features are similarly numbered. Unlike tunneling tool 110, handle 34 of tunneling tool 140 includes trigger guard 96 to prevent trigger 56 from being depressed accidently by a surgeon or other operator during a tunneling procedure.

Figures 15A, 15B, 15C:
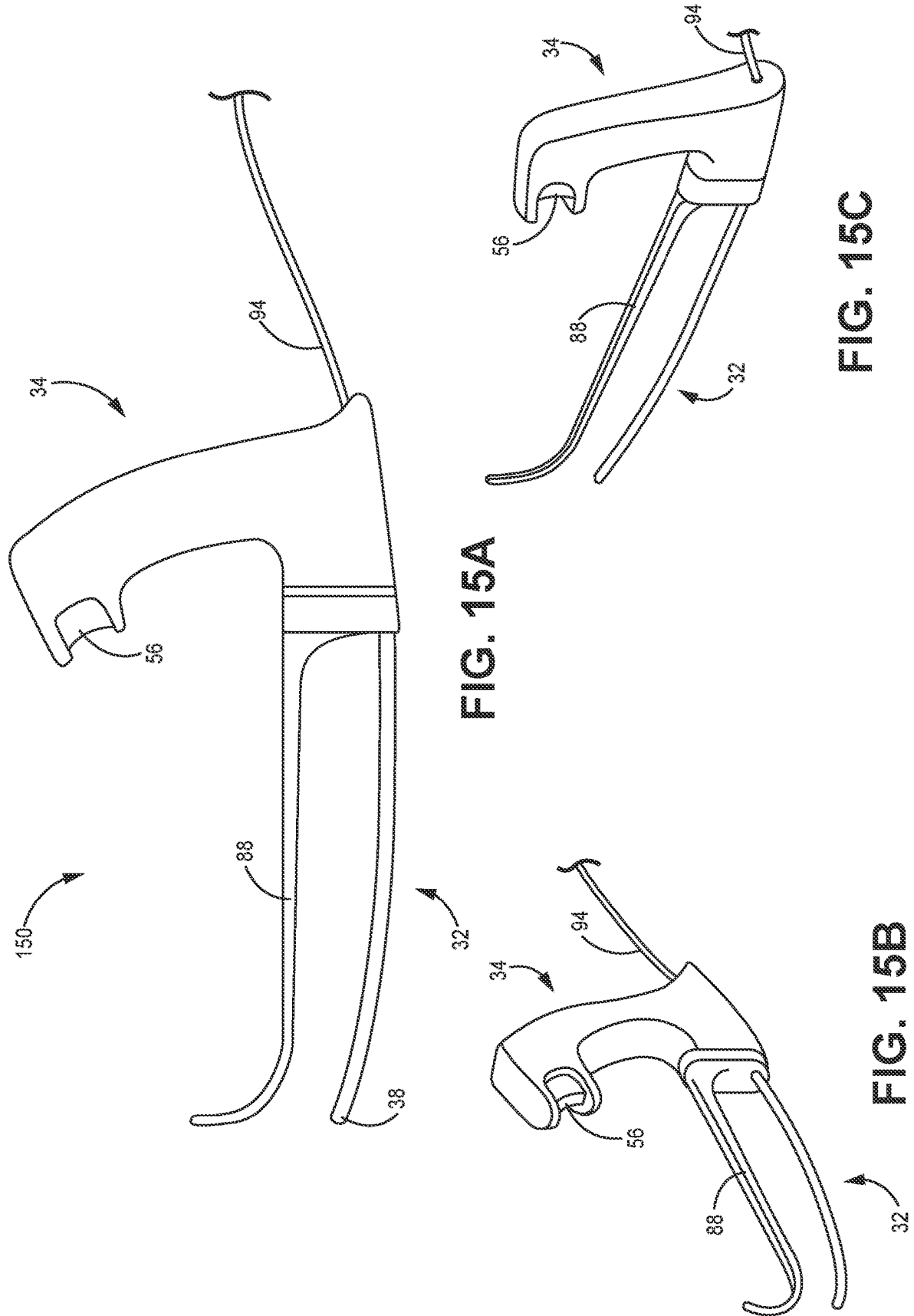
FIGS. 15A-15C are schematic diagrams illustrating another example tunneling tool according to an example of the disclosure.

FIGS. 15A-15C are schematic diagrams illustrating another example tunneling tool according to an example of the disclosure. Tunneling tool 150 may be substantially the same as tunneling tool 110 described with regard to FIGS. 11A-11E, and similar features are similarly numbered. Unlike tunneling tool 110, the vertical portion of handle 34 of tunneling tool 140 is angled further towards distal end 38 of tunneling shaft 38.

Figures 16A, 16B:
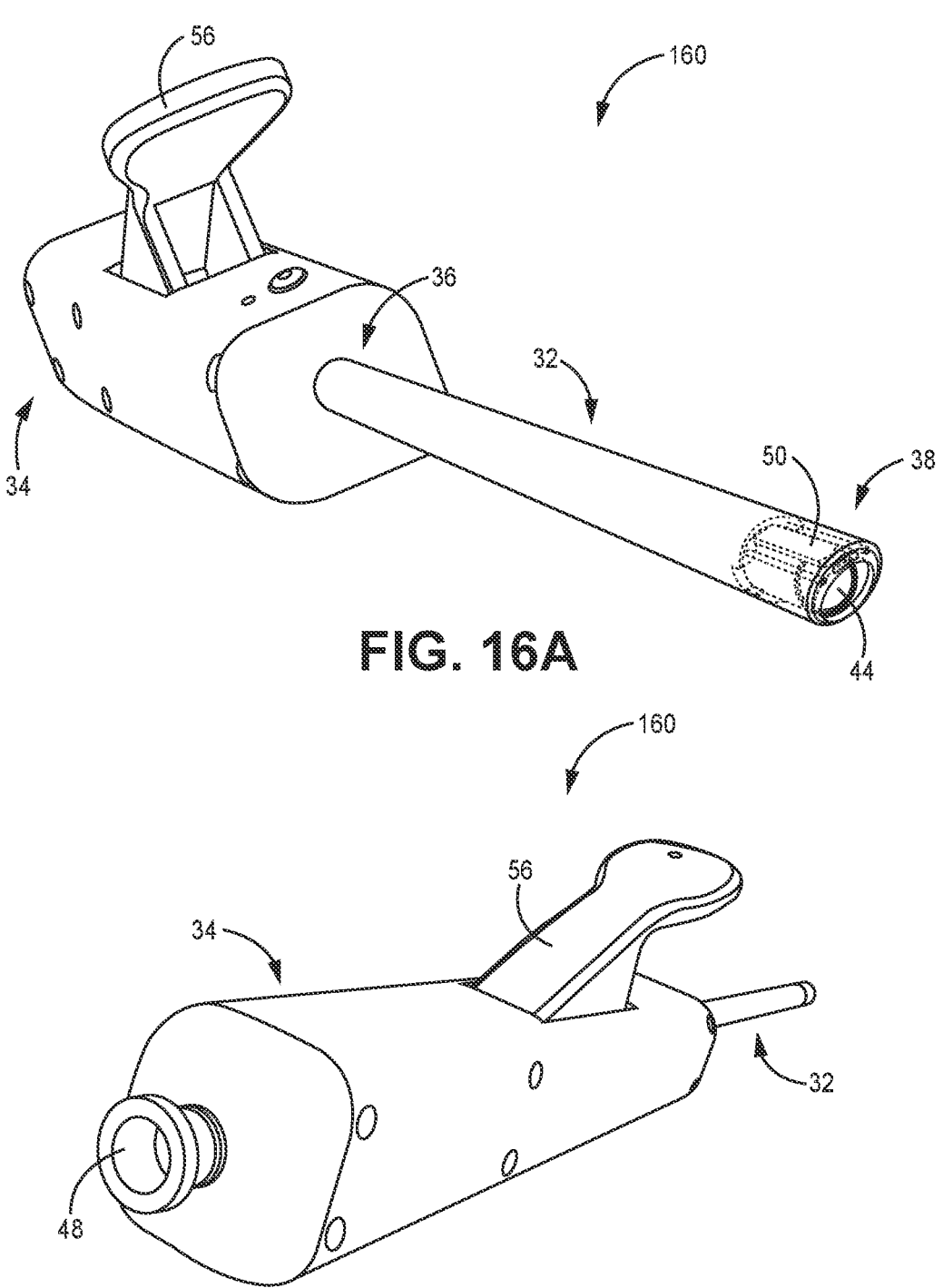
FIGS. 16A-16E are schematic diagrams illustrating another example tunneling tool according to an example of the disclosure.
Figure 16C:
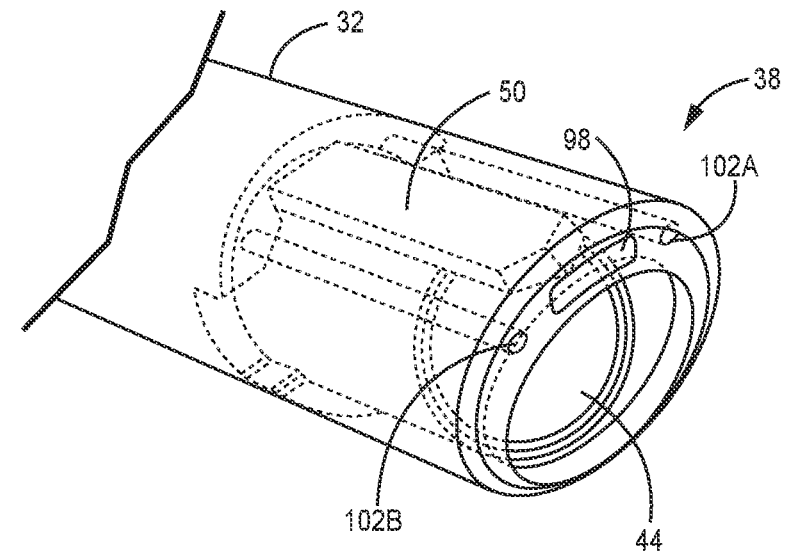
Figure 16D:
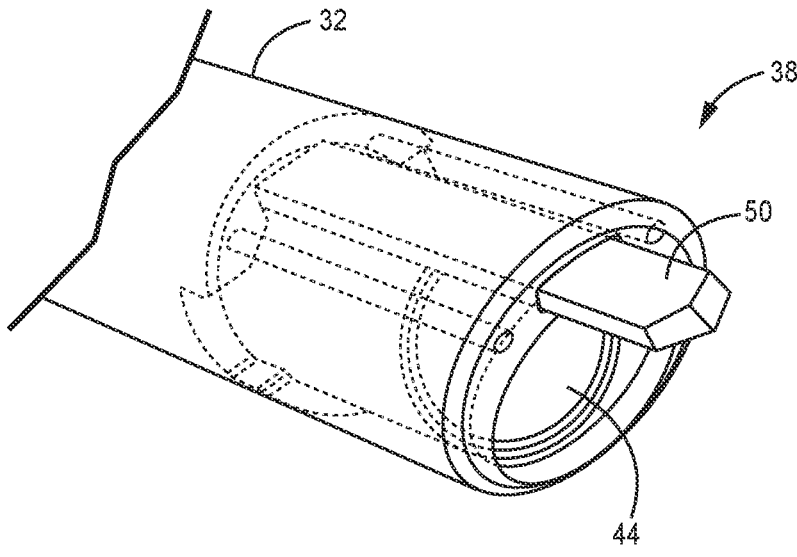
Figure 16E:
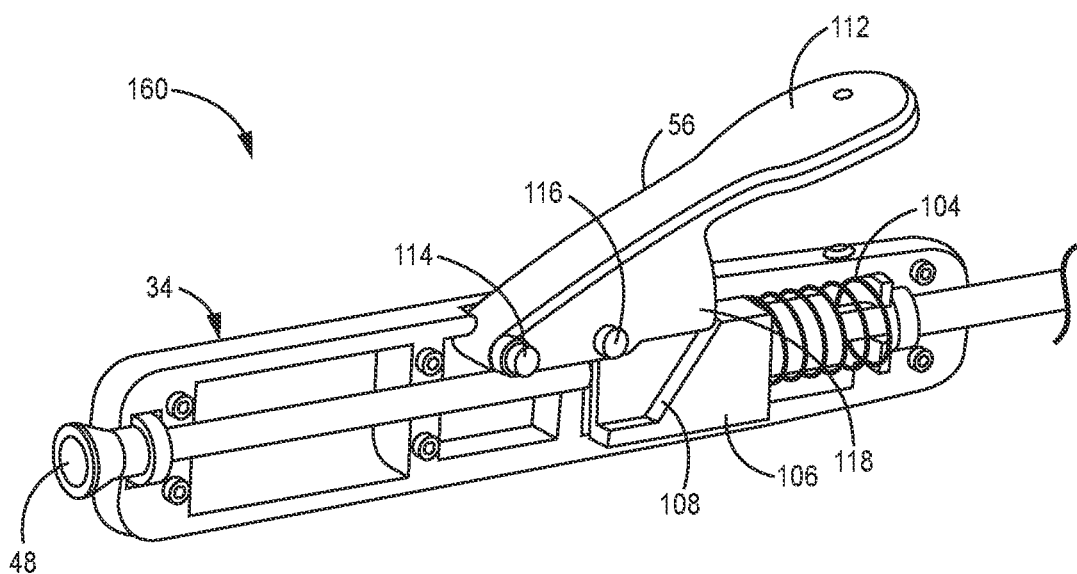

FIGS. 16A-16E are schematic diagrams illustrating another example tunneling tool 160 according to an example of the disclosure. FIGS. 16A and 16B illustrate two different perspective views of tool 160. FIGS. 16C and 16D illustrate distal end 38 of tunneling shaft 32 with optical window 44 as well as cutting tool 50 in the recessed and deployed positions, respectively. FIG. 16E illustrates a cross-sectional view of handle 34.

Figure 17:
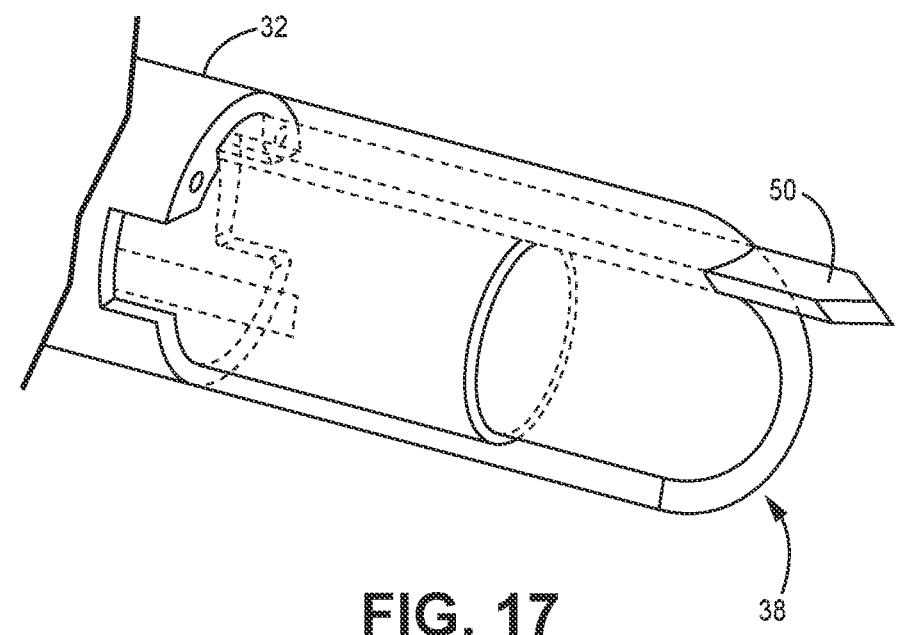
FIG. 17 is a schematic diagram illustrating the distal portion of another example tunneling tool according to an example of the disclosure.

While tunneling shaft 32 of tool 120 is substantially straight from proximal end 26 to distal end 38, in some examples tunneling shaft 32 may be curved, e.g., like that of tunneling shaft 32 of tool 30 shown in FIGS. 3-6. Tunneling shaft 32 includes inner lumen 46 that is open and may accept a rigid or flexible scope through proximal opening 48 in handle 34. Distal end 38 of tunneling shaft 32 may be made of clear or otherwise transparent material so as to enable direct visualization of the tissue through which shaft 32 is advancing. Handle 34 houses the mechanism and include trigger 56 which may extend the cutting tool 50 from a recessed (FIG. 16C) to a deployed position (FIG. 16D). Distal end 38 is generally blunt when cutting tool 50 is in a recessed position, e.g., to prevent wounding of vital organs like mammary arteries or lungs during a tunneling procedures. FIGS. 16C and 16D show distal end 38 as a beveled tip with optical window 44. However, other distal end geometries are contemplated. For example, FIG. 17 illustrates another example in which distal end 38 includes a domed or sphere-shaped tip, which may be made of a clear or otherwise transparent material.

As shown in FIG. 16C, cutting tool 50 is recessed in the channel 98 at distal end 38 when in a recessed position. Tunneling shaft 32 also includes additional lumens 102A and 102B, which may be used, e.g., for insufflation, irrigation, adding contrast, flushing lens, removing air pockets, and the like.

With reference to FIG. 16 E, proximal end 104 (which may be similar to that of blade arm(s) 54) of cutting tool is engaged to spring loaded slider 106. A sloped surface 108 of slider 106 serves as a cam. Lever 112 pivots around first post 114, and its stroke is limited by second post 116 which travels inside the slot of the handle 34. Tip 118 of the lever 112 engages the slider slope 108 to drive cutting tool 50 forward when necessary to a deployed position by depressing lever 112 of trigger 56. In such an example, cutting tool 50 may remain in a deployed position until trigger 56 is no longer depressed, e.g., as opposed to automatically retracting to a recessed position when trigger 56 is depressed.

Various examples have been described. These and other examples are within the scope of the following claims.

What is claimed is:

1. A tool comprising:
a handle;
a tunneling shaft coupled to the handle, wherein the tunneling shaft extends from a proximal end to a distal end, and at least a portion of the tunneling shaft extends in a curved orientation between the proximal end to the distal end, wherein the distal end of the tunneling shaft includes an electrosurgical tool configured to cauterize tissue, and wherein the tunneling shaft includes an inner lumen extending from the proximal end to the distal end of the tunneling shaft, and
an optical window comprised of a transparent material at the distal end of the tunneling shaft, the optical window configured to provide, to an optical tool inserted into the inner lumen, a view of a path of the distal end of the tunneling shaft.

2. The tool of claim 1, wherein the handle includes a trigger coupled to the tool, wherein depressing the trigger transfers mechanical energy to the tool to move the tool from a recessed position in which the tool is recessed into the distal end of the tunneling shaft to a deployed position in which a portion of the tool extends beyond the distal end of the tunneling shaft.

3. The tool of claim 2, further comprising at least one blade arm extending from the tool to the handle, wherein the at least one blade arm is configured to transfer the mechanical energy from the handle to the tool when the trigger is depressed.

4. The tool of claim 3, wherein the at least one blade arm includes at least two blade arms extending from the tool to the handle.

5. The tool of claim 3, wherein the at least one blade arm is configured to conduct electrical current to the tool from the handle, and wherein the tool is configured to cauterize the tissue using the current.

6. The tool of claim 5, wherein the at least one blade arm is electrically insulated within the shaft from tissue adjacent to the tunneling shaft.

7. The tool of claim 3, wherein the at least one blade arm is located adjacent to at least one of an inner surface of the tunneling shaft or an outer surface of the tunneling shaft.

8. The tool of claim 2, wherein the trigger and tool are configured such that depressing the trigger causes the tool to move from the recessed position to the deployed position, and automatically move the tool back to the recessed position.

9. The tool of claim 2, wherein, when in the deployed position, a portion of the tool extends about 0.25 millimeters (mm) to about 2 mm beyond the distal end of the tunneling shaft.

10. The tool of claim 2, wherein the distal end of the tunneling shaft is configured for blunt dissection of tissue of a patient when the tool is in a recessed position.

11. The tool of claim 1, wherein the tunneling shaft includes an extruded tube defining a plurality of inner lumens running from the proximal end to the distal end.

12. The tool of claim 1, further comprising a guide member extending from a distal end of the guide member to a proximal end of the guide member, wherein the proximal end of the guide member is coupled to the handle, and wherein the tunneling shaft extends alongside and coplanar with the guide member.

13. The tool of claim 1, wherein tunneling shaft has a length from the proximal end to the distal end of about 4 inches to about 12 inches.

14. The tool of claim 1, wherein the tunneling shaft exhibits a radius of curvature of about 15 inches to about 40 inches over at least a portion of a length of the tunneling shaft.

15. A method comprising:
inserting a distal portion of a tool in a patient through an incision in the patient, wherein the tool comprises:
a handle;
a tunneling shaft coupled to the handle, wherein the tunneling shaft extends from a proximal end to a distal end, and at least a portion of the tunneling shaft extends in a curved orientation between the proximal end to the distal end, wherein the distal end of the tunneling shaft includes a electrosurgical tool configured to cauterize tissue adjacent the distal end of the tunneling shaft, and wherein the tunneling shaft includes an inner lumen extending from the proximal end to the distal end of the tunneling shaft, and an optical window comprised of a transparent material at the distal end of the tunneling shaft, the optical window configured to provide, to an optical tool inserted into the inner lumen, a view of a path of the distal end of the tunneling shaft; and cauterizing the tissue adjacent the distal end of the tunneling shaft with the tool.

16. The method of claim 15, wherein the incision is near a xiphoid process of the patient, further comprising advancing the distal portion of the tool to an anterior mediastinum of the patient to create a sub-sternal tunnel between a sternum of the patient and a heart of the patient.

17. The method of claim 15, wherein the tunneling shaft of the tool is positioned within a lumen of an introducer sheath when inserted in the patient through the incision, the method further comprising:
withdrawing the tunneling shaft from the lumen of the introducer sheath after insertion into the patient to leave a distal portion of the introducer sheath in the patient;
inserting a medical lead within the lumen of the introducer sheath while in the patient; and
subsequently, removing the introducer sheath while in the patient to leave the medical lead in the patient.

18. The method of claim 15, wherein the handle includes a trigger coupled to the tool, the method comprising deploying the tool from a recessed position in which the tool is recessed into the distal end of the tunneling shaft to a deployed position in which a portion of the tool extends beyond the distal end of the tunneling shaft.

19. The method of claim 18, wherein the tool comprises at least one blade arm extending from the tool to the handle, wherein depressing the trigger to transfer the mechanical energy to the tool to move the tool from the recessed position to the deployed position comprises transferring the mechanical energy from the handle to the tool via the at least one blade arm.

20. The method of claim 19, wherein the at least one blade arm is configured to conduct electrical current to the tool from the handle, and wherein the tool is configured to cauterize the tissue using the electrical current.

\* \* \* \* \*